United States Patent
Hanafialamdari et al.

(10) Patent No.: US 11,612,708 B2
(45) Date of Patent: Mar. 28, 2023

(54) METHOD AND APPARATUS FOR DETERMINING AND/OR PREDICTING SLEEP AND RESPIRATORY BEHAVIOURS FOR MANAGEMENT OF AIRWAY PRESSURE

(71) Applicant: NovaResp Technologies Inc., Halifax (CA)

(72) Inventors: Hamed Hanafialamdari, Halifax (CA); Scott Lowe, Cheshire (GB); Stephen Driscoll, Halifax (CA); Luke Hacquebard, Halifax (CA); David Cecil Roach, Halifax (CA); Klaus Michael Schmidt, Halifax (CA)

(73) Assignee: NovaResp Technologies Inc., Halifax (CA)

( * ) Notice: Subject to any disclaimer, the term of this patent is extended or adjusted under 35 U.S.C. 154(b) by 0 days.

(21) Appl. No.: 17/726,719

(22) Filed: Apr. 22, 2022

(65) Prior Publication Data

US 2022/0241530 A1     Aug. 4, 2022

Related U.S. Application Data

(63) Continuation of application No. PCT/CA2021/050257, filed on Feb. 26, 2021.
(Continued)

(51) Int. Cl.
*A61M 16/00* (2006.01)

(52) U.S. Cl.
CPC ...... *A61M 16/026* (2017.08); *A61M 16/0006* (2014.02); *A61M 2016/0027* (2013.01);
(Continued)

(58) Field of Classification Search
CPC ...... G16H 50/30; A61B 5/4818; A61B 5/087; A61B 5/7264; A61B 5/7275;
(Continued)

(56) References Cited

U.S. PATENT DOCUMENTS 6,257,234 B1   7/2001   Sun
6,889,691 B2   5/2005   Eklund et al.
(Continued)

FOREIGN PATENT DOCUMENTS

EP     1844743 A2     10/2007
WO    00/010634 A1    3/2000
(Continued)

OTHER PUBLICATIONS

Czövek et al., "Tidal changes in respiratory resistance are sensitive indicators of airway obstruction in children", Thorax, 2016, 71(10): 907-915.
(Continued)

*Primary Examiner* — Victoria Murphy
(74) *Attorney, Agent, or Firm* — Tony Orsi; Bereskin & Parr LLP/S.E.N.C.R.L.s.r.l.

(57) ABSTRACT

Devices, systems and methods are provided for controlling the operation of a breathing assistance device for a user. The controller may include an input for receiving sensor data to measure at least one airflow parameter of the user's airflow; a memory unit that stores at least one machine learning model and at least one classifier or predictor; and a processor that is configured to perform measurements and to generate a control signal for adjusting the operation of the breathing assistance device for a current monitoring time period by: obtaining measured air pressure and/or airflow data and measured FOT data during a current monitoring time period; performing feature extraction on the measured data to obtain feature values that are used by the machine learning model
(Continued)

employed by the at least one classifier or predictor to determine a property of the user; and adjusting the control signal based on the determined property.

20 Claims, 16 Drawing Sheets

Related U.S. Application Data

(60) Provisional application No. 62/981,541, filed on Feb. 26, 2020.

(52) U.S. Cl.
CPC .............. *A61M 2016/0033* (2013.01); *A61M 2205/6009* (2013.01); *A61M 2230/04* (2013.01); *A61M 2230/14* (2013.01); *A61M 2230/202* (2013.01); *A61M 2230/205* (2013.01); *A61M 2230/46* (2013.01); *A61M 2230/60* (2013.01)

(58) Field of Classification Search
CPC ....... A61B 5/0816; A61B 5/4809; A61B 5/08; A61B 5/0823; A61B 5/4812; A61B 5/4815; A61B 5/4836; A61B 5/7282; A61M 16/026; A61M 16/0006; A61M 2016/0027; A61M 2016/0033; A61M 2205/6009; A61M 2230/04; A61M 2230/14; A61M 2230/202; A61M 2230/205; A61M 2230/46; A61M 2230/60
See application file for complete search history.

(56) References Cited

U.S. PATENT DOCUMENTS

| | | | | |
|---|---|---|---|---|
| 7,680,537 | B2* | 3/2010 | Stahmann | A61N 1/36514 607/42 |
| 7,942,824 | B1 | 5/2011 | Kayyali et al. | |
| 8,973,578 | B2 | 3/2015 | Dellaca'et al. | |
| 9,358,417 | B2 | 6/2016 | Meyer et al. | |
| 9,668,673 | B2 | 6/2017 | Gobbi et al. | |
| 10,537,463 | B2 | 1/2020 | Kopelman | |
| 11,077,282 | B2 | 8/2021 | Kwok | |
| 11,229,765 | B2 | 1/2022 | Bayer et al. | |
| 2005/0043644 | A1* | 2/2005 | Stahmann | A61B 5/0816 600/529 |
| 2005/0081847 | A1* | 4/2005 | Lee | A61N 1/36514 607/9 |
| 2005/0085866 | A1* | 4/2005 | Tehrani | A61N 1/36132 607/42 |
| 2005/0256420 | A1* | 11/2005 | Norman | A61B 5/4818 600/533 |
| 2007/0215156 | A1* | 9/2007 | Kwok | A61F 5/56 128/205.24 |
| 2008/0072896 | A1 | 3/2008 | Setzer et al. | |
| 2008/0257349 | A1* | 10/2008 | Hedner | G16H 20/40 128/204.23 |
| 2011/0251985 | A1 | 10/2011 | Waxman et al. | |
| 2014/0283834 | A1 | 9/2014 | Ahmad et al. | |
| 2014/0350426 | A1 | 11/2014 | Lehrman et al. | |
| 2014/0371635 | A1* | 12/2014 | Shinar | G08B 21/0211 600/595 |
| 2015/0119743 | A1 | 4/2015 | Maksym et al. | |
| 2015/0320338 | A1 | 11/2015 | Kane et al. | |
| 2016/0045154 | A1 | 2/2016 | Addison et al. | |
| 2016/0106341 | A1 | 4/2016 | Adam et al. | |
| 2018/0117270 | A1 | 5/2018 | Bassin | |
| 2019/0217030 | A1 | 7/2019 | Burgess et al. | |
| 2020/0046923 | A1 | 2/2020 | Hanafialamdari | |
| 2022/0023561 | A1 | 1/2022 | Hanafialamdari et al. | |

FOREIGN PATENT DOCUMENTS

| | | |
|---|---|---|
| WO | 2011/006199 A1 | 1/2011 |
| WO | 2013/067580 A1 | 5/2013 |
| WO | 2015/127377 A8 | 8/2015 |
| WO | 2015/138474 A1 | 9/2015 |
| WO | 2017/136639 A1 | 8/2017 |
| WO | 2019/030632 A1 | 2/2019 |

OTHER PUBLICATIONS

International Search Report and Written Opinion dated Feb. 5, 2020 in International Patent Application No. PCT/CA2019/051604 (10 pages).
International Search Report and Written Opinion dated Jan. 4, 2018 in International Patent Application No. PCT/CA2017/051258 (11 pages).
Mochizuki et al., "Forced Oscillation Technique and Childhood Asthma", Allergology International, Sep. 2012, 61(3): 373-383.
Dellacà et al., "Detection of expiratory flow limitation in COPD using the forced oscillation technique", Eur. Respir. J., Feb. 2004, 23(2): 232-240.
Non-Final Office Action and Notice of References Cited dated Jan. 28, 2022 in U.S. Appl. No. 16/342,724 (6 pages).
International Search Report and Written Opinion dated May 11, 2021 in International Patent Application No. PCT/CA2021/050257 (8 pages).
Extended European Search Report dated Jul. 13, 2022 in EP Patent Application No. 19881164.8 (18 pages).
Abdeyrim et al., "What can impulse oscillometry and pulmonary function testing tell US about obstructive sleep apnea: a case-control observational study?", Sleep Breath., Mar. 2016 (online pub: May 10, 2015), 20(1): 61-68.
Non-Final Office Action and Notice of References Cited dated Sep. 1, 2022 in U.S. Appl. No. 17/292,667 (15 pages).
Non-Final Office Action and Notice of References Cited dated Jul. 22, 2022 in U.S. Appl. No. 17/726,719 (8 pages).

\* cited by examiner

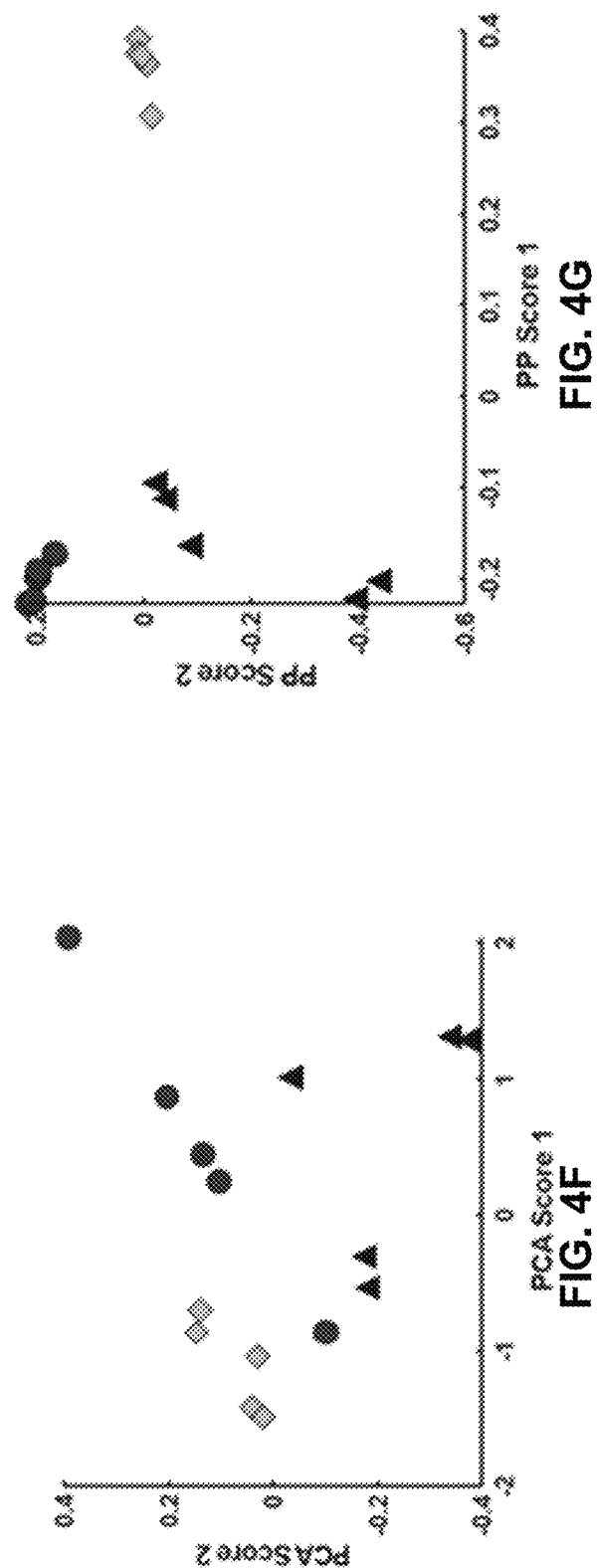
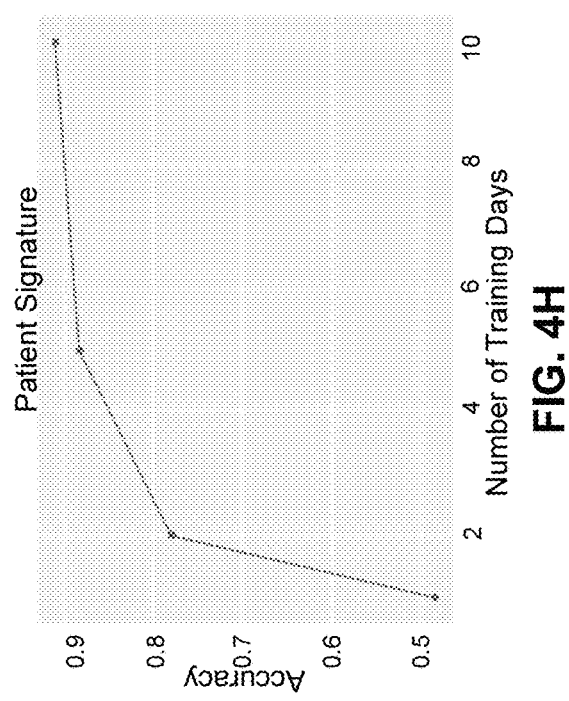
FIG. 4G
FIG. 4H
FIG. 4F

METHOD AND APPARATUS FOR DETERMINING AND/OR PREDICTING SLEEP AND RESPIRATORY BEHAVIOURS FOR MANAGEMENT OF AIRWAY PRESSURE

CROSS-REFERENCE TO RELATED APPLICATION

This application is a continuation of International Patent Application No. PCT/CA2021/050257 filed Feb. 26, 2021, which claims the benefit of U.S. Provisional Patent Application No. 62/981,541 filed Feb. 26, 2020 and the entire contents of each of which are hereby incorporated herein in their entirety.

FIELD

Various embodiments are described herein for an apparatus and method that may be used to operate a breathing device to provide breathing assistance to a user of the breathing device through determining and/or predicting different sleep and/or respiratory behaviours.

BACKGROUND

Individuals suffering acute or chronic respiratory (Chronic Obstructive Pulmonary Disease (COPD), asthma, Acute Respiratory Distress Syndrome (ARDS)) or respiratory-related conditions (e.g. sleep apnea) may require assistive devices to maintain respiratory functions at normal levels. Assistive devices such as mechanical ventilators, Positive Airway Pressure (PAP) devices or Continuous Positive Airway Pressure (CPAP) devices are common to provide breathing assistance. However, while such assistive devices are critical with respect to maintaining normal respiratory functions, these devices may also cause harm and distress to a user as a result of the stress or strain due to the amount of pressure or flow imparted on the user's respiratory system. Moreover, all devices are currently reactive and not proactive to predict and prevent respiratory distress or discomfort. As such, there is a desire for methods and systems to identify and minimize user harm.

It is known in the art that there are various levels of mechanical support for different sorts of respiratory failure. In the most basic form the inspired concentration of oxygen may be increased to percentages above 21% which is the normal atmospheric content of oxygen. This helps a patient in need to satisfy the metabolic need of oxygen for their body.

The next higher level of ventilatory support addresses the problem of when the oxygen content of the inhaled gas mixture is not sufficient to keep the homeostasis of the patient's body. This means that also retention of $CO_2$ is becoming a problem. For these sorts of respiratory failures a more invasive way of ventilation including active elevation of the airway pressure above the atmospheric pressure is involved to eliminate $CO_2$ as the end product of the metabolism of the body. As this involves a tightly fitting mask, there are limits to the pressure that can be applied to the system.

If elevation of inhaled oxygen and increase of airway pressure facilitated by the mask is no longer sufficient then so called mechanical ventilation using an intratracheal tightly fitted tube and/or tracheostomy along with a ventilator is used for ventilation. The parameters that are controlled with a ventilator include the volume of each breath applied to the patient, the respiratory rate per minute which, when taken together, allow for the volume of ventilation of the patient to be controlled along certain time intervals, e.g. every minute. In addition, typically mechanical ventilation also controls for the fraction of inhaled oxygen from 21% to 100% in air and the inspiratory to expiratory ratio of the breathing cycle. If these measures are not sufficient to keep blood oxygen and $CO_2$ levels within safe physiological limits then opposed end expiratory pressure (PEEP) and an I/E inspiratory to expiratory ratio is applied. As far as monitoring of ventilation is concerned there are a variety of methods known in the art that include end tidal $CO_2$, inspired $CO_2$, inspired $O_2$, expired $O_2$, blood gas analysis of arterial blood pressure/volume diagrams and volumetric measures of the inspired and expired volumes of ventilation in the patient.

In sleep apnea, the "gold standard" diagnostic test for Obstructive Sleep Apnea (OSA) is polysomnography (PSG), in which respiratory, cardiac, muscular, and neurological parameters are monitored during sleep. The monitoring of these various physiological and neurological parameters allow for the evaluation of oxygen saturation of the blood, pauses of ventilation, EEG activity for determination of sleep phase, and EMG for determination of spontaneous muscular activity.

SUMMARY OF VARIOUS EMBODIMENTS

In accordance with the teachings herein there are provided various embodiments for an apparatus and method that may be used to operate a breathing device to provide breathing assistance to a user of the breathing device through determining and/or predicting different sleep and/or respiratory behaviours. For examples, different sleep and respiratory behaviours include different sleep stages, breathing signatures and predicted sleep disruption severity.

In a broad aspect, in accordance with the teachings herein, there is provided a controller for controlling the operation of a breathing assistance device that provides breathing assistance to a user, wherein the controller comprises: an input for receiving sensor data to measure at least one airflow parameter of the user's airflow; a memory unit that comprises software instructions and parameters for at least one machine learning model and at least one classifier or predictor; and a processor that is electronically coupled to the input to receive the sensor data, the processor being configured to perform measurements and to generate a control signal for controlling the breathing assistance device for a current monitoring time period by: obtaining measured air pressure data and/or measured airflow data and optionally measured FOT data during the current monitoring time period when the user is using the breathing assistance device; performing feature extraction on the measured data to obtain feature values; applying the feature values to the at least one machine learning model employed by the at least one classifier or a predictor to determine a property of the user; and adjusting the control signal based on the determined property of the user.

In at least one embodiment, the processor is configured to execute a breathing signature classifier that applies a breathing signature machine learning model to the feature values to determine a current breathing signature for the user.

In at least one embodiment, the processor is configured to stop operation of the breathing assistance device when the current breathing signature does not match a stored breathing signature for a rightful user of the breathing assistance device.

In at least one embodiment, the processor is configured to execute a sleep stage classifier that applies a sleep stage machine learning model to the feature values to determine a sleep stage classification index for the user.

In at least one embodiment, the processor is configured to adjust the operation of the breathing assistance device based on the determined sleep stage classification index.

In at least one embodiment, the processor is configured to execute a predictive sleep disruption severity detector that applies a predictive sleep disruption severity machine learning model to the feature values to determine a predicted sleep disruption severity index for the user.

In at least one embodiment, the processor is configured to adjust the operation of the breathing assistance device based on the predicted sleep disruption severity index.

In another aspect, in accordance with the teachings herein, there is provided a system for providing breathing assistance to a user, wherein the system comprises: a breathing assistance device that generates an airflow comprising at least one pressure impulse or a continuous pressure flow rate; an entry element that is coupled to the breathing assistance device and is worn by the user to provide the airflow to the user during use; and a breathing assistance device controller that is defined in according with one or more of the embodiments described herein.

In another aspect, in accordance with the teachings herein, there is provided a method for adjusting an airflow provided by a breathing assistance device to a user, wherein the method comprises: receiving sensor data for measuring at least one airflow parameter of the user's airflow; receiving the sensor data, at a processor and using the processor for performing measurements and generating a control signal for controlling the breathing assistance device for a current monitoring time period by: obtaining measured air pressure data and/or measured airflow data and optionally measured FOT data during the current monitoring time period when the user is using the breathing assistance device; performing feature extraction on the measured data to obtain feature values; applying the feature values to a machine learning model employed by a classifier or a predictor to determine a property of the user; and adjusting the control signal based on the determined property of the user.

In at least one embodiment, the method comprises executing a breathing signature classifier that applies a breathing signature machine learning model to the feature values to determine a current breathing signature for the user.

In at least one embodiment, the method comprises stopping operation of the breathing assistance device when the current breathing signature does not match a stored breathing signature for a rightful user of the breathing assistance device.

In at least one embodiment, the method comprises executing a sleep stage classifier that applies a sleep stage machine learning model to the feature values to determine a sleep stage classification index for the user.

In at least one embodiment, the method comprises adjusting the operation of the breathing assistance device based on the determined sleep stage classification index.

In at least one embodiment, the method comprises executing a predictive sleep disruption severity detector that applies a predictive sleep disruption severity machine learning model to the feature values to determine a predicted sleep disruption severity index for the user.

In at least one embodiment, the method comprises adjusting the operation of the breathing assistance device based on the predicted sleep disruption severity index.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIGS. 4F and 4G are plots of principal component analysis scores and projection pursuit analysis, respectively, with the two projection vectors having the largest variance determined from respiratory data obtained for three different patients plotted along the x and y axes respectively and showing that each patient has a unique data clusters (i.e. unique breathing signatures).

FIG. 4H is a plot showing the accuracy of a patient breathing signature classifier versus training days for data obtained from 18 patients.

Figure 1:
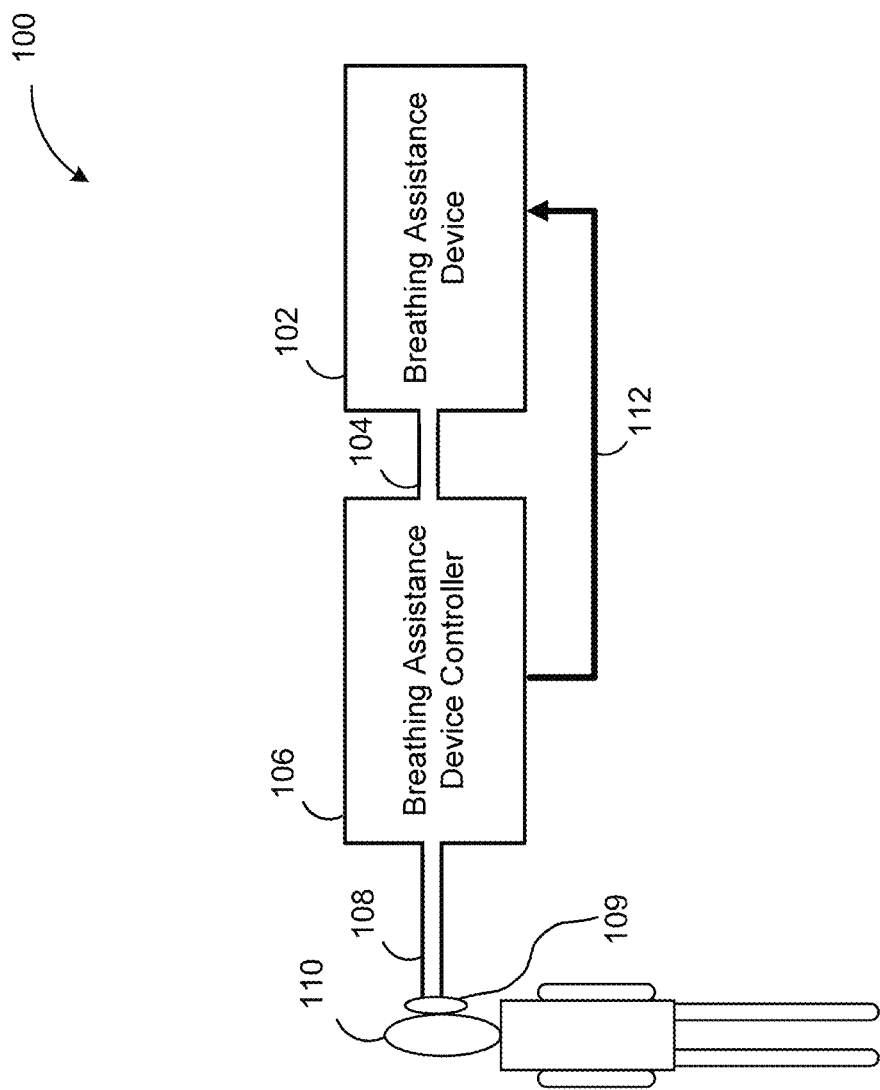
FIG. 1 is a block diagram of an example embodiment of a breathing assistance system for controlling or tuning a breathing assistance device during use by a user based on determining and/or predicting different sleep and/or respiratory behaviours in accordance with the teachings herein.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices or methods having all of the features of any one of the devices or methods described below or to features common to multiple or all of the devices and or methods described herein. It is possible that there may be a device or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, fluidic or electrical connotation. For example, as used herein, the terms coupled or coupling can indicate that two elements or devices can be directly connected to one another or connected to one another through one or more intermediate elements or devices via an electric signal, an electrical connection, a mechanical element, a fluid or a fluid transport pathway, for example, depending on the particular context.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term such as, but not limited to, 1%, 2%, 5% or 10%, if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as, but not limited to, 1%, 2%, 5% or 10%, for example.

The example embodiments of the devices, systems or methods described in accordance with the teachings herein may be implemented as a combination of hardware and software. For example, the embodiments described herein may be implemented, at least in part, by using one or more computer programs, executing on one or more programmable devices comprising at least one processing element and at least one storage element (i.e. at least one volatile memory element and at least one non-volatile memory element). The hardware may comprise one or more input devices including one sensor, a touch screen, a keyboard, a mouse, buttons, keys, sliders or any combination thereof, as well as one or more output devices including an output port for transmitting a control signal, a display, a speaker, a printer, or any combination thereof depending on the implementation of the hardware.

It should also be noted that there may be some elements that are used to implement at least part of the embodiments described herein that may be implemented via software that is written in a high-level procedural language such as object oriented programming. The program code may be written in C++, C #, JavaScript, Python, or any other suitable programming language and may comprise modules or classes, as is known to those skilled in object-oriented programming. Alternatively, or in addition thereto, some of these elements implemented via software may be written in assembly language, machine language, or firmware as needed. In either case, the language may be a compiled or interpreted language.

At least some of these software programs may be stored on a computer readable medium such as, but not limited to, a ROM, a magnetic disk, an optical disc, a USB key, and the like that is readable by a device having a processor, an operating system, and the associated hardware and software that is necessary to implement the functionality of at least one of the embodiments described herein. The software program code, when read by the device, configures the device to operate in a new, specific, and predefined manner (e.g., as a specific-purpose computer) in order to perform at least one of the methods described herein.

At least some of the programs associated with the devices, systems, and methods of the embodiments described herein may be capable of being distributed in a computer program product comprising a computer readable medium that bears computer usable instructions, such as program code, for one or more processing units. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g., downloads), media, digital and analog signals, and the like. The computer useable instructions may also be in various formats, including compiled and non-compiled code.

It should be noted that the term "user" covers a person who is using a breathing assistance device. In some cases, the user may be an individual that is using the breathing assistance device in their home or a non-medical setting. In other cases, the user may be a patient who is using the breathing assistance device in a medical setting such as a clinic or a hospital, for example.

Oscillometry, also known as the forced oscillation technique (FOT), may be performed within the field of respiratory diagnostics by superimposing fluctuations on airway pressure while a user is breathing normally and measuring the resultant pressure and flow rate to determine the mechanical properties of the user's respiratory system. For example, the measured pressure and flow rate may then be used to determine the mechanical impedance of the user's respiratory system. This mechanical impedance is the ratio of the oscillatory pressure to the flow rate in the frequency domain, which can be expressed as a complex quantity (having real and imaginary components) as a function of frequency. More specifically, the real part of the mechanical impedance may be regarded as the respiratory system resistance ($R_{rs}$) and the imaginary part can be regarded as the respiratory system reactance ($X_{rs}$). FOT is commonly used in modern CPAP machines as a method to differentiate between obstructive and central apnea events, using FOT frequencies of 1-5 Hz.

When the complex mechanical impedance of the respiratory system is described, it is generally common to present the average $R_{rs}$ and average $X_{rs}$ behavior over a frequency range of interest. These average values can normally be computed from averaging impedance values estimated using frequency domain methods such as by performing Fourier transforms on the measured pressure and flow values taken from multiple finite overlapping time windows, or from averaging over a time course computed from recursive time domain methods that can also effectively examine short duration overlapping time periods.

However, the inventors have previously determined temporal variations that occur in $R_{rs}$ and in $X_{rs}$ during respiration may contain information related to an individual's breathing and their respiratory system. The temporal variations for the $R_{rs}$ and the $X_{rs}$, which can be denoted as $R_{var}$ and $X_{var}$ respectively, can be determined using a frequency domain technique such as the short-time-Fourier transform (STFT) or the Wavelet transform. Although it has been established that variations in the amplitude of $X_{var}$ between inspiration and expiration contains signs of respiratory health, the inventors have previously determined that there is a linkage between the $R_{var}$ and the $X_{var}$ when they are being determined using FOT and $R_{var}$ and $X_{var}$ are changing over time.

For example, it is known that variations in resistance are increased in asthmatic patients and that variations in reactance increase in COPD patients. However, the inventors have previously discovered that some of these variations in reactance for COPD patients leak into variations in resistance and the inventors have also previously discovered that both of these may be taken into account for more accurate diagnosis and monitoring. The inventors have also previously found that the same situation occurs with asthmatic patients where variations in reactance leak into variations in resistance and both the reactance and the resistance need to be included in diagnosis and decision making for more effective treatment.

Therefore, conventional technologies that monitor $R_{rs}$ and $X_{rs}$ separately may be missing essential information about the health of the individual's lungs. However, as previously determined by the inventors there are situations in which $R_{var}$ and $X_{var}$ may be monitored and the linkage between $R_{var}$ and the $X_{var}$ may be used to determine certain situations such as when a person, for whom the $R_{var}$ and the $X_{var}$ are determined, has a particular breathing signature, when the person is in a certain sleep stage, when the person is experiencing respiratory failure, predicting the sleep disruption severity for the person when a respiratory event is about to occur or any combination thereof. This has not been previously determined by others in this field.

A respiratory failure may be understood to cover all diseases and conditions which can result in a negative change in a person or animal's respiratory system such as a breathing obstruction or small airways. In some cases, the respiratory failure may be a temporary respiratory event that occurs such as during OSA or an asthma attack or it may be due to a chronic respiratory condition such as lung cancer, cystic fibrosis or chronic obstructive pulmonary disease.

In accordance with the teachings herein, there is provided various embodiments for intelligently monitoring, analyzing, and determining and/or predicting different respiratory and sleep behaviours such as determination of patient breathing signature, determining of patient sleep stage classification, prediction of sleep disruption severity for a patient or any combination thereof. The methods involve using machine learning and other advanced computational techniques to build accurate supervised classification and prediction models. Some of these models will employ measurements of either: (a) air pressure and air flow only; (b) FOT measured airway impedance only; (c) plethysmography such as EEG or (d) a combination of two or more of (a), (b) and (c).

The inventors have previously determined that the link or relationship between $R_{var}$ and the $X_{var}$ can be used to determine a respiratory index that is used to detect when respiratory failure is occurring and in such cases to take corrective actions to help the individual to breathe more normally again. The actions may include, but are not limited to, various techniques that are applied to keep the user's airway open to avoid hypo-oxygenation or hypocapnia in the user's blood. For example, for a COPD patient, when the combination of $X_{var}$ and $R_{var}$ shows a respiratory failure the breathing assistance device may be controlled to adjust its inspiratory and expiratory pressures. In addition, the breathing assistance device may be controlled to change the mixture of gases provided to the patient (e.g. in COPD there may be a change in the concentration of oxygen provided to the patient) to also help mitigate that specific disease. The index may be a combination of $R_{var}$ and $X_{var}$.

However, in accordance with the teachings herein, the respiratory index may be combined with a sleep stage classification index and/or a predicted sleep disruption severity index to improve the effectiveness of the breathing assistance device.

In at least one embodiment, the combination may be based on comparing the separate indexes to corresponding threshold levels to perform the corrective action with a higher degree of confidence to compensate for an already occurring respiratory event.

Alternatively, in at least one embodiment, these indices may be combined to generate a combined index which can then be used to determine whether to perform the corrective action with a higher degree of confidence. Conventionally, this has never been done and advantageously this may be used to improve the respiratory health status of the individual in a shorter period of time.

The link or relationship between $R_{var}$ and $X_{var}$ can be determined using a benchtop lung simulator made using physical elements an example of which is described in U.S. provisional patent application No. 62/758,394 entitled "BENCHTOP WITHIN-BREATH DYNAMIC LUNG SIMULATOR" and filed on Fri, Nov. 9, 2018 and in U.S. non-provisional patent application Ser. No. 16/678,153 entitled "BENCHTOP WITHIN-BREATH DYNAMIC LUNG SIMULATOR", filed on Fri, Nov. 8, 2019 and published as US patent application publication number US20200152089A1 on May 14, 2020, the entirety of each of which is hereby incorporated by reference.

The inventors have also previously determined that the link or relationship between $R_{var}$ and the $X_{var}$ can be used along with the measurement of certain physiological and/or neurological parameters to determine a respiratory index that can be used to predict when respiratory failure will occur and in such cases to take corrective actions to reduce the chances that the individual will experience the respiratory failure that was predicted or at least reduce the intensity of the respiratory failure. For example, the changes in $R_{var}$ and $X_{var}$, and therefore the change in $Z_{var}$, and their weighted versions $R_{var,w}$, $X_{var,w}$ and $Z_{var,w}$, can be correlated with a physiological measurement (e.g. CO2) and/or a neurological measurement (e.g. EEG) to predict when respiratory failure will happen. In this case, the corrective actions are proactive to avoid respiratory failure which is in contrast with the respiratory detection technique described previously which is reactive in nature since corrective action is only taken after the individual starts experiencing respiratory failure. However, in accordance with the teachings herein, the respiratory index may be combined with a sleep stage classification index and/or a predicted sleep disruption severity index to improve the effectiveness of the breathing assistance device. In at least one embodiment, the combination may be based on comparing the separate indexes to corresponding threshold levels to perform the proactive corrective action with a higher degree of confidence to compensate for an already occurring respiratory event. Alternatively, in at least one embodiment, these indices may be combined to generate a combined index which can then be used to determine whether to perform the proactive corrective action with a higher degree of confidence. Conventionally, proactive corrective actions based on prediction has never been done and advantageously this may be used so that the individual's respiratory health status does not worsen and/or stays within acceptable limits.

In either of the aforementioned aspects that incorporate performing corrective actions, depending on the indices that are determined, which are generally numbers, the operating parameters of the breathing assistance device may then be adjusted to ensure that the user of the breathing assistance device does not experience respiratory failure or at least experiences minimal respiratory failure. Accordingly, at least one of these indices can be used to generate a feedback control signal that is used to control the operation of the breathing assistance device. These indices may be determined for a given time period during which many numbers are generated which can be collectively referred to as the respiratory index signal. The respiratory index signal can be used to control the breathing assistance device over the given time period.

Therefore, in one aspect, the teachings herein provide for real time determination of a user's breathing signature, classification of the user's sleep stage and/or classification of predicted sleep disruption severity which may then be used to perform at least one of adjusting the operation of the breathing assistive device and providing data in a user report that can be used to monitor the breathing of the user and/or diagnose a respiratory disorder for the user. For example, the report can be determined for data collected when the user slept at night and the report can be provided to the user or a medical professional for review, such as in the morning, so that the user or the medical professional can review data about their respiratory and sleep health, for example.

In accordance with another aspect, the teachings provide for the real time assessment of lung mechanics to detect respiratory failure, or to predict respiratory failure when at least one other physiological signal is measured, based on the determination of a respiratory index and comparison of the respiratory index to a normative values, which may be represented by a threshold in at least some cases and also incorporating a sleep stage classification index and/or a predicted sleep disruption severity index in the analysis of the respiratory index for determining whether to take a corrective action or proactive correction action with a higher degree of confidence. The respiratory index, sleep stage classification index and the predicted sleep disruption severity index can be continuously determined and used to continuously manage the settings of a breathing assistance device to reduce, mitigate or avoid the respiratory failure.

Previously it was not possible to predict the respiratory failure of the user of a breathing assistance device in an automated fashion before the respiratory failure was about to occur. Accordingly, breathing assistance devices were conventionally controlled in a manual fashion by a medical practitioner who set and then adjusted the operational parameters of the breathing assistance device every so often. This was detrimental since if the user started experiencing respiratory failure it was not conventionally possible to automatically adjust the breathing assistance device to reduce the effect or amount of respiratory failure encountered by the user which may be fatal in some situations where response time is critical for adjusting the operation of the breathing assistance device. Furthermore, such conventional techniques will not even allow for the prediction of imminent respiratory failure.

More recently, other techniques including traditional FOT/Oscillometry have been used to automatically adjust the parameters of breathing assistance devices. However, traditional FOT uses averaging and therefore there is a delay of multiple seconds before any detection can happen. This is also detrimental to the user health when a significant respiratory failure is imminent or is occurring. Moreover automatic adjusting of breathing assistance devices utilizing techniques such as only sensing the airflow or oxygen levels may not provide enough information of the health of the complete respiratory system in certain situations.

It is believed that the techniques of determining one or more of the respiratory, sleep stage and predictive sleep disruption severity indices of a user of a breathing assistance device and generating a control signal to control the breathing assistance device to maintain the respiratory health of the user in a certain range where the user is not experiencing respiratory failure, in accordance with the teachings herein, will increase the rate of adoption of use of breathing assistance devices where the use is voluntary (i.e. as for sleep apnea devices). This method also provides technical advantages such as an increase in the speed of adaptation of the breathing assistance device to any respiratory failure encountered or soon to be encountered by the user as the methods can detect or predict the respiratory failure relatively quickly, with increased confidence, and can also take reactive or proactive steps quickly to control the breathing assistance device to reduce the level/amount of respiratory failure that is encountered by the user or prevent the respiratory failure from even happening. This can be critical in some cases where increased respiratory failure can have significant, if not fatal, consequences to the user.

Referring now to FIG. 1, illustrated therein is a block diagram of a breathing assistance system 100 for performing at least one of determining breathing signature, performing sleep stage classification and predicting sleep disruption severity. In at least one embodiment, the breathing assistance system 100 can also be used for controlling or tuning a breathing assistance device using the forced oscillation technique based on detection and/or prediction of respiratory failure in accordance with at least one embodiment of the teachings herein. The system 100 comprises a breathing assistance device 102 that generates an airflow that is provided to a user 110 via air transport pathways 104 and 108 and, for example, a laryngeal tube, a breathing mask or an endotracheal tube 109 (hereinafter collectively referred to as an "entry element"). The airflow can be at least one pressure pulse of air, a continuous flow of air, or a superposition of pressure pulses of air and a continuous flow of air. The airflow is controllable by adjusting at least one of the air pressure and flow rate of the breathing assistance device 102 via corresponding input controls on the breathing assistance device 102.

In some embodiments, the breathing assistance device 102 may be a mechanical ventilator for providing breathing support to the user. In other embodiments, the breathing assistance device 102 may be a CPAP, APAP, BiPAP or PAP device for providing breathing support to the user. In other embodiments, the breathing assistance device 102 may be a respiratory treatment delivery device such as, but not limited to, respiratory treatment delivery devices that assist a user in clearing their lungs and coughing out secretions. In other instances the breathing assistance device 102 may be an anesthesia machine in the OR, an ICU ventilator, a home ventilator and oxygenator of COPD, and any other machine that provides breathing assistance to a user who has a respiratory disease. Therefore, in general, the teachings described herein for the detection and/or prediction of respiratory failure and the proactive or reactive actions that are taken to reduce, remove or pre-empt respiratory failure can be used with all types of ventilation including invasive (with tube) and non-invasive (tubeless) ventilation.

A breathing assistance device controller 106 is coupled to the breathing assistance device 102 via the air transport pathway 104 (which may also be called the flow passage 104) and receives airflow from the breathing assistance device 102 and delivers the airflow via the air transport pathway 108 and the entry element 109 to the user 110. It should be noted that the term "air" in the present disclosure is used generally to denote the flow of gas and other airborne particles through the system 100. For example, the output of a mechanical ventilator may include gasses and/or vapors other than air such as, but not limited to, anesthetics, for example which are typically vapors but can also be gases. In a PAP device, water vapor may be combined with air. In some embodiments of the breathing assistance device 102, gaseous medication (i.e. steroids, oxygen, Nitrogen, etc.) may be added to the air flow and provided to the patient under ventilation based on respiratory health and/or measured comfort level. For example, the medication may include an appropriate amount of steroids that may be used daily to improve the CPAP experience for the user. The airflow may be delivered to the user 110 via the entry element 109. In the present embodiment, the entry element 109 may be a mask worn over the user's 110 nose and mouth, just over the nose or adjacent or inside the nostrils of the user 110 for alternative masks. In other embodiments, the entry element 109 may be an endotracheal tube inserted into the trachea by means of intubation or tracheostomy.

In embodiments in which the breathing device 102 is a mechanical ventilator, there are actually two air pathways (not shown) instead of just the air transport pathway 104 (which may also be called a flow passage) where one of the pathways is used for inhalation and the other of these pathways is used for exhalation. The pathways shown in FIG. 1 apply for the case where the breathing assistance device 102 is a PAP device. It may be thus understood that the breathing assistance device 102 provides at least one pathway to allow air to flow from the air transport pathway 104 to the air transport pathway 108. It may further be understood that there can be embodiments in which the breathing assistance device controller 106 is at least partially or completely incorporated "inline" with the airflow pathways from the breathing assistance device 102 to the user 110.

In the present example embodiment, the breathing assistance device controller 106 comprises one or more sensors (not shown) to measure various parameters of the airflow being delivered to the user 110. For example, sensors can be attached to the mask worn by the user 110 which may result in ideal SNR for the sensor data obtained from the sensors. Alternatively, the sensors, such as ultrasonic sensors for example, can be attached in the tubing pathway. In either case, these sensors can be used to measure airflow parameters associated with both inspiration and expiration. However, in the case of a PAP machine, such sensors are located close to the mask because the tube 108 only carries an inspiratory flow whereas in a mechanical ventilator the sensors can be attached to the mask or endotracheal tube or they can be located anywhere along the tubes that are used for the inspiratory pathway and the expiratory pathway.

In some embodiments, the breathing assistance device controller 106 may not include these sensors but may instead read these parameters from the breathing assistance device 102 since the breathing assistance device 102 may also be equipped with sensors for measuring airflow parameters.

The breathing assistance device controller 106 may further comprise a device to provide a forced oscillation signal, in order to provide changes in air pressure for the airflow provided to the user 110. In some embodiments, a sensor for measuring both air pressure and airflow is present. In other embodiments, dedicated sensors may be used to measure the airflow or the air pressure such that more than one sensor may be used with the breathing assistance device controller 106. For example, some sensor technologies use a laser to detect movement or ultrasound can be used to detect both pressure and flow rate using one sensor (as the measured flow rate can be determined from dividing the measured pressure by a known resistance).

The measured airflow parameters such as air volume, air pressure and airflow rate may be used by the breathing assistance device controller 106 to generate a control signal 112 that can be used as feedback to adjust the operation of the breathing assistance device 102. For example, the breathing assistance device controller 106 can employ a control method, where the control signal that is generated may be based on determining the breathing signature of the user according to method 300 (see FIG. 4A), determining the sleep stage for the user such as in method 350 (see FIG. 5), and/or determining a predicted sleep disruption severity such as in method 400 (see FIG. 6A). In other embodiments there can be methods that, for example, performs detection of when respiratory failure will occur and then uses a sleep stage classification index and/or a predicted sleep disruption severity index, such as in method 450 (see FIG. 7) to generate the control signal to provide a corrective action so that the user no longer experiences the respiratory failure.

Alternatively, in some embodiments, the breathing assistance controller 106 can employ a control method that incorporates a sleep stage classification index and/or a predicted sleep disruption severity index, such as method 500 (see FIG. 8) or method 600 (see FIG. 9A), for example, to predict when respiratory failure will occur (e.g. perhaps up to and including the next few minutes such as for example from about a few milliseconds up to about 5 minutes) and to then generate the control signal to provide a proactive action so that the user does not experience the predicted respiratory failure. In such embodiments, additional measured signals can be used to implement the predictive method. For example, the additional measured signals can be one or more of the physiological or and/or neurological signals that are obtained during polysomnography (PSG) and hereafter referred to as PSG signals. The PSG signals may include at least one physiological signal (such as but not limited to eye movements (EOG), muscle activity or skeletal muscle activation (EMG) and cardiac signals (ECG)) and/or at least one neurological signal (such as but not limited to EEG). Sensors for measuring such signals are not shown in FIG. 1 but such sensors are known by those skilled in the art and can be added into the system 100.

In both of the detection and prediction embodiments, the control signal 112 may be used to adjust one, two, a few or all of the adjustable parameters of the breathing assistance device 102 to prevent or reduce the severity of a respiratory failure event. For example, parameters that may be adjusted include the flow rate of the airflow, the volume of the airflow, the pressure of the airflow, the frequency of certain changes in the airflow (like changes in the flow rate, volume, pressure and amplitude of the airflow), the amplitude of the airflow and/or the phase of the airflow that can be generated by the breathing assistance device 102.

Figure 2:
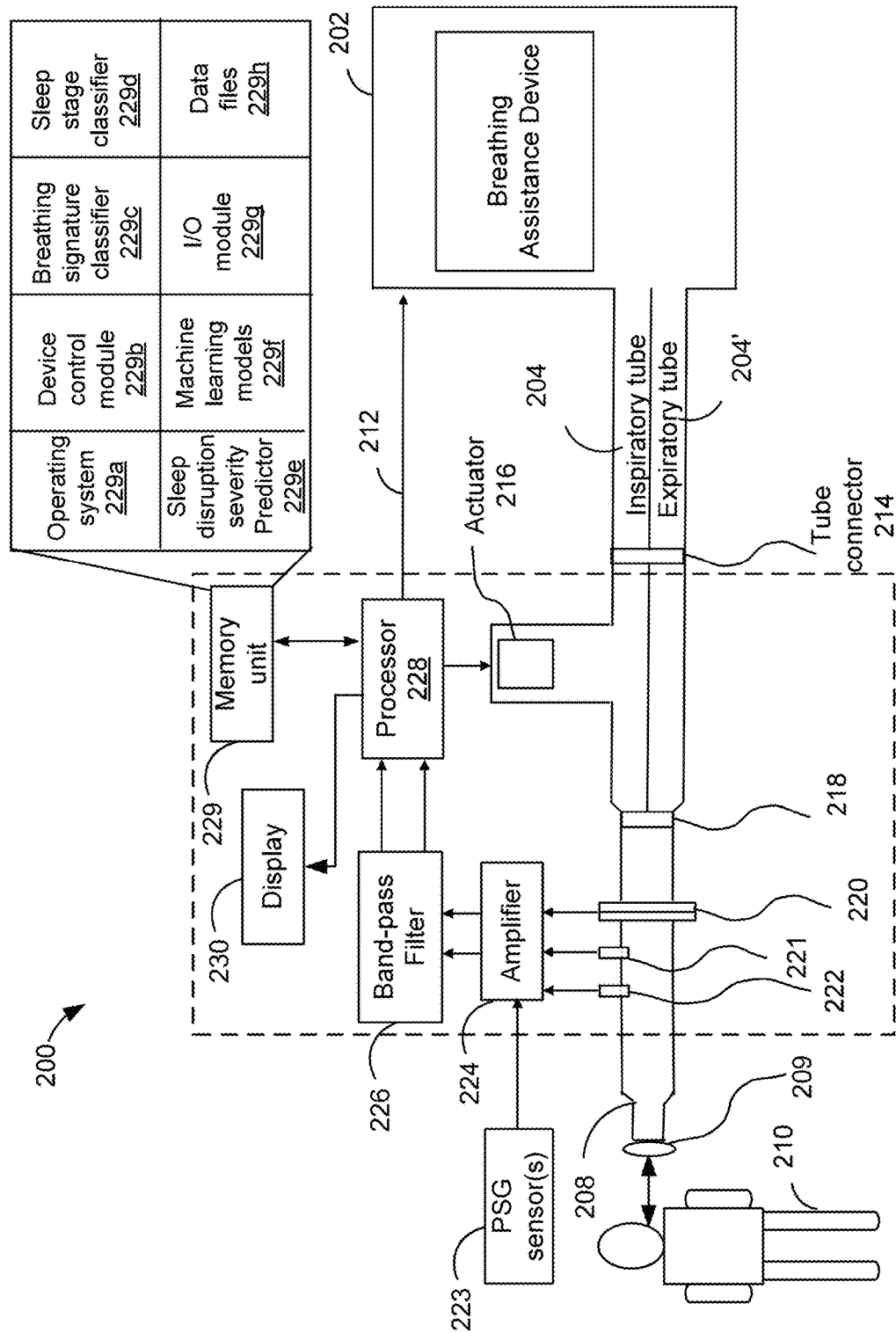
FIG. 2 is a block diagram of another example embodiment of a breathing assistance system for controlling or tuning a breathing assistance device during use by a user based on determining and/or predicting different sleep and/or respiratory behaviours in accordance with the teachings herein.

Referring now to FIG. 2, shown therein is a block diagram of an example embodiment of a breathing assistance system 200 for determining a breathing signature, a sleep stage classification index and/or a predicted sleep disruption severity index and potentially using one or more of these items for controlling or tuning a breathing assistance device 202 during use by a user 210 based on detection and/or prediction of respiratory failure in accordance with the teachings herein. Elements in FIG. 2 that correspond to elements in FIG. 1 have been numbered similarly. Similar to the configuration of the breathing assistance system 100, a breathing assistance device 202 generates airflow that is provided to a user 210 via air transport pathways 204 and 204' and the breathing tube 208 and the airflow is monitored by a breathing assistance device controller 206 for modifying the operation of the breathing assistance device 202 under certain conditions. Similar to FIG. 1, the airflow may be delivered to the user 210 via an entry element 209. In this example embodiment the entry element 209 may be a mask worn over to fluidically couple with the user's 210 nose (i.e. nostrils) and optionally the user's mouth. In other embodiments, the entry element 209 may be an endotracheal tube inserted into the trachea by means of intubation or tracheostomy.

FIG. 2 provides additional details with respect to the various system components that may be employed. In some embodiments, the breathing assistance device 202 may be a mechanical ventilator for providing breathing support. In other embodiments, the breathing assistance device 202 may be a PAP device for providing breathing support. Other options are available for the breathing assistance device 202 as explained for the breathing assistance device 102.

In the present embodiment, the breathing assistance device 202 is a mechanical ventilator and includes an inspiratory tube 204 and an expiratory tube 204' for providing an airflow pathway for airflow leaving and returning to the breathing assistance device 202, respectively. The inspiratory tube 204 and the expiratory tube 204' may be connected to the breathing assistance device controller 206 at one airflow pathway using the tube connector 214. The airflow may then flow to the user 210 through another airflow pathway of the breathing assistance device controller 206. The airflow from the inspiratory tube 204 may be subjected to perturbation from a forced oscillation produced by a motor or an actuator (hereinafter referred to as an "actuator" to refer to both cases) 216 generating an oscillation of air at a desired frequency and intensity. The actuator 216 may be one of a loud speaker, an electromagnet, a piezoelectric device, a piston and a motor, for example. The choice of actuator may be dependent on the design specifications such as the physical size of the device 206 as well as on the limitations imposed on the Bill of Materials (BOM). It should be noted that in some embodiments, the actuator 216 can be included in the breathing assistance device 202 and not in the breathing assistance device controller 206. Alternatively, in some embodiments, both the breathing assistance device 202 and the breathing assistance device controller 206 can include separate actuators.

The oscillation pressure signal has an oscillation frequency that may be at any frequency that is practical for performing air pressure and airflow measurements during FOT measurement. For example, the frequency may include, but is not limited to the range of about 0.001 Hz to about 100 MHz or even up to 1 THz. In some embodiments, the frequency range is from a lower frequency of about 5 Hz, 10 Hz, or 20 Hz to an upper frequency of about 100 MHz or 1 THz. In some embodiments, the frequency range is from about 40 Hz to an upper frequency of about 100 MHz or 1 THz. In some embodiments, the frequency is about 37 Hz or about 79 Hz where harmonics of these frequencies will not interfere with one another during FOT measurement. In some embodiments, a multi-frequency signal can be used having different harmonics. For example, the oscillation signal may be a square wave or a triangular wave, each having several frequency components. A multi-frequency signal is useful in certain situations such as when impedance is calculated at different frequencies. The oscillation pressure signal is superimposed into the modified and/or spontaneous breathing of the user 210.

In some embodiments, the generated oscillation pressure signal may also be controlled to deliver a desired pressure. In some cases, it may be preferable to produce pressures (i.e. amplitude of the generated oscillation signal) that do not exceed a peak-to-peak value of about 0.01 cm $H_2O$ to about 2 cm $H_2O$. In some other cases, the pressure may be chosen on the basis of the frequency of oscillation or on the sensitivity and precision of the flow rate sensor and/or the pressure sensor. In some cases, the amplitude of the oscillation (i.e. the pressure) may follow an inverse frequency trend (1/f). For example, if frequencies of about 6, 11 and 19 Hz are used, the amplitude of pressure at about 6 Hz is higher than the amplitude of pressure at about 11 Hz. Similarly, the amplitude of pressure at about 11 Hz is higher than the amplitude of pressure at about 19 Hz.

The inspiratory tube 204 and the expiratory tube 204' may be combined prior to reaching the user 210 at a junction using a tube fitting 218 connected to a breathing tube 208. Subsequent to the tube fitting 218, the combined airflow may be sensed to determine airflow parameters such as the airflow rate and the air pressure. In this example embodiment, a sensing system is used that comprises a flow transducer 220 and a pressure transducer 221. It should be noted that the flow transducer 220 may also be called a flow rate transducer or an airflow transducer. The sensor type used for the transducers 220 and 221 can be any appropriate transducer device, including but not limited to, ultrasonic, pneumatic or piezoelectric transducers, for example. In some embodiments, the airflow parameters can be measured and calculated by recording the pressure drop across a pneumotachograph, which is used as the sensor.

The outputs of the flow transducer 220 and the pressure transducer 221 may be preconditioned prior to being further processed and analyzed. For example, the output signals from the transducers 220 and 221 may be amplified by an appropriate amplifier 224 to obtain the desired signal amplitudes. For example, in some embodiments, the amplifier 224 may be a lock-in amplifier which may be used to reduce signal noise to help focus on the frequency of interest. It should be noted that separate amplifiers can be used for each measured signal or a dual channel amplifier may be used.

The amplified signal may then be filtered to remove extraneous frequency domain information. In the present embodiment, a band-pass filter 226 with a tuned center-frequency corresponding to the frequency of the oscillation produced by the actuator 216 may be used. In some embodiments, the passband may be made sufficiently narrow such that a notch filter can be used when a single frequency is used for FOT. The band-pass filter 226 has a narrow passband but it is preferably large enough to contain any side lobes in the measured signals that contain modulated breathing information.

After the signals have been amplified and filtered, the signals are received by the processor 228 for further processing and analysis in order to determine one or more aspects of the user such as, but not limited to: (1) a breathing signature, (2) a sleep stage classification and/or a sleep stage classification index, and/or (3) prediction of sleep disruption severity and/or a predicted sleep disruption severity index. In at least one embodiment, a respiratory index may also be generated. The processor 228 can then generate a control signal 212 based on at least one of these aspects that have been determined and the control signal 212 is provided to the breathing assistance device 202 to adjust its operation, as described in more detail below.

In some embodiments, the processor 228 may a programmable device such as a programmable microcontroller or a field programmable gate array (FPGA). In other embodiments, the processor 228 may be part of a single-board computer system platform such as the Arduino platform, or Raspberry Pi platform. In yet other embodiments, there may be more than one processor which is used when significant data requires processing. In yet other embodiments, the signal filtering may be performed using the processor 228 such as by using digital signal processing (DSP) techniques such that a separate filtering device 226 may not be necessary.

The control signal 212 can be provided to the breathing assistance device 202 using any method known to those skilled in the art. For example, the control signal 212 can be provided through a wired connection. However, in other implementations, the control signal may be communicated wirelessly to the breathing assistance device 202 in which case the system 200 can include a transmitter or a transceiver (such as a WiFi or Bluetooth transceiver).

The measured airflow parameters, indices and/or control signal 212 may also be shown on an optional display 230 provided on the breathing assistance device controller 206. The display 146 may be, but is not limited to, an LCD display such as that for a tablet device or smartphone.

The system 200 also includes a memory unit 229 which can include RAM, ROM, one or more hard drives, one or more flash drives or some other suitable data storage elements such as disk drives, etc. The memory unit 229 stores program instructions for an operating system 229a, a device control module 229b, one or more of a sleep stage classifier 229d, a breathing signature classifier 229c, and/or a sleep disruption severity predictor 229e, machine learning models 229f, an input/output (I/O) module 229g, and one or more data files 229h. Other software instructions may be included as is known to those skilled in the art.

The device control module 229b comprises software instructions that, when executed, configures the processor 228 to operate in a particular manner to implement various functions, processes, and methods for the system 200. For example, the device control module 229b can include program instructions for sensing various data from the sensors 220-223, performing various calculations using the sensed data and then executing one or more of the breathing signature classifier 229c, the sleep stage classifier 229d, the sleep disruption severity predictor 229e and the machine learning models 229f to determine one or more indices from which control signals may be generated in order to perform: (1) controlling the breathing assistance device 202, and/or (2) generating certain data about the respiratory and/or sleep characteristics of the user which can then be included in a report and/or analyzed to monitor and/or diagnose the user for certain conditions.

The breathing signature classifier 229c is used to determine the breathing signature using respiratory data that is sensed by one or more of sensors 220-222 and in some cases determined from the sensed data for a particular user 210 based on using a machine learning model or an analytical approach. The breathing signature classifier 229c is described in more detail with respect to method 300 in FIG. 4A.

The sleep stage classifier 229d is used to determine the sleep stage that the user 210 is in using respiratory data that is sensed by one or more of the sensors 220-222 and in some cases determined from the sensed data for a particular user 210 based on using a machine learning model. A sleep stage classification index may also be defined based on the sleep stage classification that is determined. The sleep stage classifier 229d is described in more detail with respect to method 350 in FIG. 5.

The sleep disruption severity predictor 229e is used to predict the severity of an upcoming sleep disruption event using respiratory data that is sensed by one or more of the sensors 220-222 and in some cases determined from the sensed data for a particular 210 user based on using a machine learning model. A predicted sleep disruption severity index may also be defined based on the predicted sleep disruption severity. The sleep disruption severity predictor 229e is described in more detail with respect to method 400 in FIG. 6A.

The machine learning models 229f include different types of models that are used for classifying or predicting different sleep or breathing related phenomena. The machine learning models 229f may be based on using different machine learning methods such as one or more of a Random forest classifier, a logistic linear classifier, the K-Nearest Neighbors algorithm, the Feature-Based Dissimilarity Space Classifier (FDSC), Neural Networks and support vector machines. In an alternative embodiment, deep learning or Convolutional Neural Networks (CNN) may be used. For reduced computational time, it may be preferable to use a Random forest classifier as the machine learning model.

Certain input features are provided to the machine learning model that have high predictive power. For example, the input features may include the Power Spectral Density (PSD) of the measured air flow (e.g. airflow and airflow rate are synonymous). The PSD may be measured over the entire spectral range of the sampled sensor data. Alternatively, there may be cases where the PSD over a more specific frequency range may be measured such as between about 0.01 Hz to about 20 Hz which contains most of the information for the PSD. Other potential input features may include one or more of the PSD of the measured air pressure, the PSD of the measured resistance and reactance using FOT, and for a given PSD, the number of peaks in the PSD, and the power at a certain frequency. In other cases, the input features for a given measured or determined signal may be one or more of an index of mass quantile for the signal; a windowed linear least squares regression coefficients along the signal; the absolute energy of the signal (e.g. the sum of the squared amplitudes of the signal); the min and/or max amplitude of the signal; the standard deviation, skewness, and/or kurtosis of the signal; the number of peaks in the signal; the autocorrelation of the signal and the absolute value of the FFT coefficients of the signal. The signal may be the measured air flow, the measured air pressure, the reactance obtained from the FOT method, the resistance obtained from the FOT method or the impedance obtained from the FOT method. The actual input features depend on the particular type of machine learning model (i.e. breathing signature, sleep classification or predictive sleep disruption severity).

The machine learning models may be trained in various ways. For example, data that was obtained from patients was preprocessed (as described herein for FIG. 2) and divided into a training set, a testing set and a validation test. For example, the training set, the test set and the validation test may comprise using amounts of the data in the proportion of 70%, 15% and 15%, respectively. The training data is used to train the machine learning model so that it accurately predicts a desired parameter. The machine learning model was initialized with some initial parameters and then trained using the training set to determine that machine learning model parameters and input features that provided the highest accuracy. The machine learning model was then tested with the test data set and the accuracy was noted. The parameters of the machine learning model were then adjusted to maximize the accuracy of the machine learning model on the test data set. The machine learning model was then tested with the validation data set and the accuracy was noted.

The data used to develop, test and validate the machine learning models described herein was obtained from 33 patients in an approved study conducted at the QEII Health Sciences Centre in Halifax. The patients were 47% female and 53% male with the median age being 55.5 years and the median nights of CPAP use being 135 nights. The test data included thousands of sleep apneas of various categories including obstructive, central and hypopnea sleep apnea. The data was split into test, training and validation data sets. Obstructive sleep apnea events were extracted from the data (for intensity), baseline (normal breathing) and pre-apnea periods (for intensity prediction). Data was also taken based on different EEG determined sleep stages. The data includes measured pressure of air flow, measured air flow rate, and determined resistance and reactance using the measured pressure and air flow rates while performing the FOT method at different frequencies including 4 Hz, 17 Hz, 43 Hz and 79 Hz. The data also included PSG measurements.

The input/output module 229g receives input data that was obtained by the sensors, preprocesses the input data, and/or generates outputs data (or signals such as control signal 212 from processing done by the device control module 229b) that are then sent to the corresponding hardware. The input/output module 229g may, for example, operate in conjunction with the device control module 229b to communicate data (or signals) between one or more of the processor 228 and one or more of the sensors 220 to 223 and the display 230. The functionality of the input/output module 229g may be implemented, for example, using a combination of hardware, firmware, and/or software.

The data files 229h may store any temporary data (e.g., data that is not needed after the breathing assistance device 202 has been used or permanent data (e.g., data saved for later use), such as user data (e.g., a user ID), settings for the breathing assistance device 202, and preprocessing or other processing settings including variables and calibration data. The data files 229h may also include various user data for each user that uses the breathing assistance device 202 such as identification data, respiratory physiological data and recorded user data during use of the breathing assistance device 202.

In at least one embodiment, the breathing assistance device controller 206 can be configured to operate continuously to monitor the pressure and flowrate of the airflow provided to the user 210 to allow for determining the user's breathing signature, performing sleep stage classification and/or predicting sleep disruption severity which may be used in various ways including for constant adjustment of the operation of the breathing assistance device 202. Doing so may permit real-time or near real-time adaptive adjustments to be made to minimize or avoid any respiratory failure that is experienced by the user 210. In other embodiments, the breathing assistance device controller 206 may alternatively be controlled to operate intermittently, for example, at a set time interval such as every 30 seconds or every 60 seconds. Such operating conditions may be preferred if the breathing assistance device controller 206 is battery operated so as to help extend the operational lifetime of the breathing assistance device 202.

In embodiments in which the system 200 is used to predict when the user 210 will soon experience respiratory failure, the sensing system may also include at least two additional sensors including a gas sensor 222 and one or more sensors used in PSG which are collectively referred to as PSG sensors 223. The gas sensor 222 can be a CO2 gas sensor. The PSG sensors 223 can include one or more sensors that are used to obtain at least one physiological signal and/or at least one neurological signal. For example, the physiological signals include one or more of ECG, EOG, and EMG signals and the neurological signals include one or more of EEG and Peripheral Neurophysiological Examination (PNE) signals. These signals can be measured using known electrodes that are placed at certain locations on the user 210 as is known by those skilled in the art. The CO2 signal is also a physiological measurement that can be obtained. The PSG signals can also be pre-processed as is known by different channels of the amplifier 224 and the band-pass filter 226 to reduce noise for these particular signals before these signals are sent to the processor 228 for further analysis. The settings for the amplification and filtering of the PSG signals are known to those skilled in the art. In embodiments which only detect respiratory failure and take reactive actions the gas sensor 222 and the PSG sensor(s) 223 are not included in the system 200.

Figure 3:
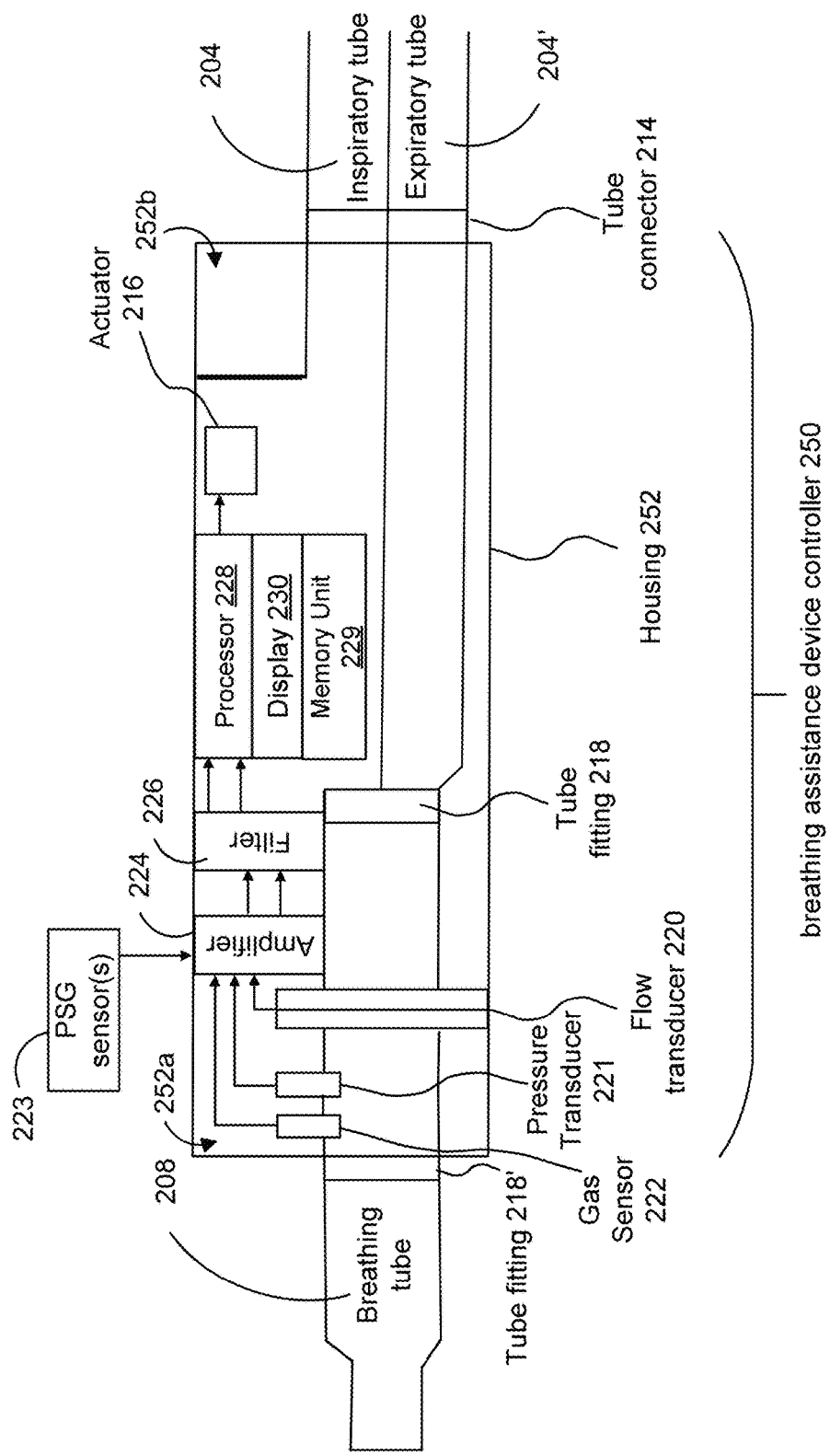
FIG. 3 is a block diagram of an example embodiment of a breathing assistance device controller that can be used with the breathing assistance system.

FIG. 3 shows an example embodiment of an integrated breathing assistance device controller 250 in which the various components needed for monitoring airflow and controlling the breathing assistance device 202 are fitted within a single device so as to allow the device to be used physically "inline" with the breathing assistance device 202. Hence the breathing assistance device controller 250 can be referred to as an inline device. The references numerals shown in FIG. 3 generally correspond to those described previously for components that are similar in in FIGS. 2 and 3.

Furthermore, in embodiments in which the integrated breathing assistance device controller 250 is used in the prediction of when the user 210 will experience respiratory failure, the controller 250 also includes the gas sensor 222 and it can be coupled to the PSG sensor(s) 223. In some embodiments the signals measured by the PSG sensor(s) 223 can be wirelessly transmitted to the integrated breathing assistance device controller 250 which will include a wireless communication radio or short range communication module such as a BlueTooth module (both not shown), for example. Accordingly, in embodiments which only detect respiratory failure and take reactive actions the gas sensor 222 and the PSG sensor(s) 223 may not be included in the integrated breathing assistance device controller 250.

The breathing assistance device controller 250 has a housing 252 with first and second ends 252a and 252b. The end 252b can be fitted to the inspiratory tube 204 and the expiratory tube 204' via a tube connector 214. The end 252a may be attached to the breathing tube 208 using a tube fitting 218' to provide ventilation to the user 210. It should be noted that the junction (i.e. tube connector 214) that joins the inspiratory tube 204 and the expiratory tube 204' is internal to the device 250, and the tube fitting 218 is also internal to the device 250. Therefore, in some embodiments, the breathing assistance device controller 206 can be regarded as an enhanced tube adaptor to fit, connect or join breathing tube 208 to the inspiratory tube 204 and the expiratory tube 204'. However, it should be noted that there is no expiratory tube 204' when the breathing assistance device controller 250 is used with a CPAP machine as expiration is vented to the atmosphere in this case.

Figure 4A:
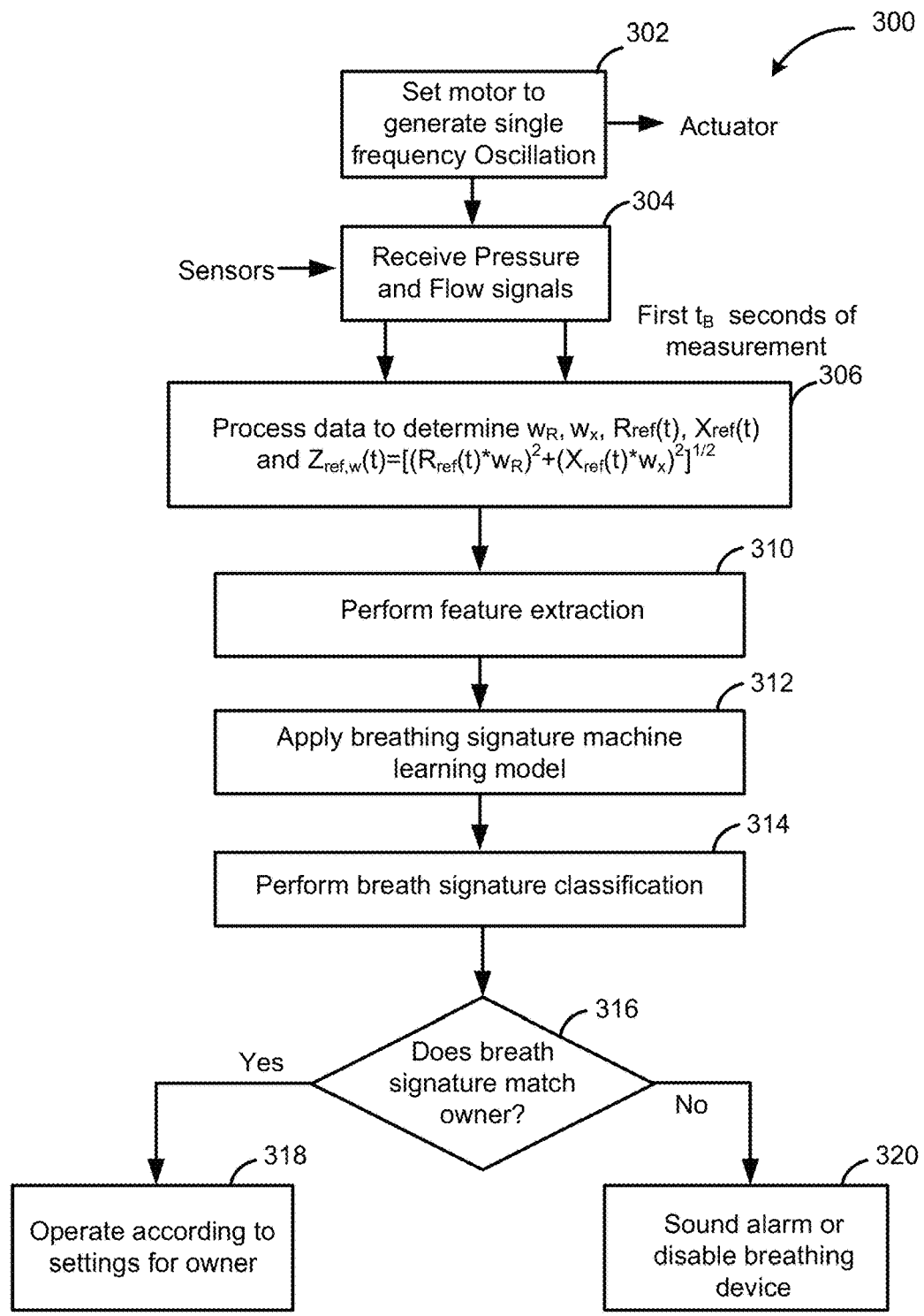
FIG. 4A is a flowchart of an example embodiment of a sleep signature detection method that utilizes patient breathing signature determination to control the operation of a breathing assistance device in accordance with the teachings herein.

Referring now to FIG. 4A, shown therein is a flowchart depicting an example embodiment of a sleep signature detection method 300 that can be used to acquire pressure and airflow measurements and use the measurements to determine the breathing signature determination of the user/patient to control the operation of a breathing assistance device to stop or reduce the severity of the user's respiratory failure. In particular, method 300 employs machine learning to identify people based of their unique breathing patterns and respiratory mechanics. This may be based of measurements of airway pressure, airflow and/or measurements of airway impedance using FOT. For ease of explanation, the elements depicted in the breathing assistance system 200 shall be used in describing the various steps of the method 300. For example, the method 300 may be implemented by the processor 228 of the breathing assistance system 200. However, it should be understood that this technique can be used on the integrated breathing assistance device controller 250 or another applicable device.

The method 300 may begin when the breathing assistance device 202 has been activated, and is supplying an airflow to the user 210. Starting at act 302, the processor 228 may operate the actuator 216 (e.g. motor) to generate an oscillation pressure signal having one or more oscillation frequencies within a desired frequency range. For example, in some embodiments the desired frequency range can be any frequency between about 0.01 Hz to about 1 THz. As mentioned previously, the oscillation may be a single frequency oscillation. However, in other embodiments, the oscillation pressure signal may comprise a number of oscillation frequencies (i.e. where the oscillation is not sinusoidal). Act 302 can be done on a continuous or periodic basis as explained previously.

At act 304, sensors coupled to the breathing assistance device controller 206, such as the flow transducer 220 and the pressure transducer 221, measure the flow rate and pressure, respectively, of the airflow (including the perturbation) that is sent to the user 210. The detected signals may be amplified by the amplifier 224 and filtered by, in this case, band-pass filter 226 with a center-frequency corresponding the frequency of the oscillation produced by the actuator 216. Also noted previously, in some embodiments, the passband may be made sufficiently narrow such that a notch filter can be used instead when a single frequency is used in the FOT measurement.

After the signals have been processed by applying amplification and filtering, the processed signals are received by the processor 228 for further processing and analysis. At act 306 the processor 228 may use the measured signals to determine the volume V(t) of the airflow and the mechanical impedance of the user's respiratory system over time. The volume V(t) may be determined as the integral of the flow rate signal that is measured plus a known bias or constant volume. To determine, the mechanical impedance, the processor 228 can apply a windowing function to the processed flow rate and pressure signals to help enforce periodicity (i.e. to reduce leakage in the frequency domain) and subsequently perform the Fourier transform (e.g. via the fast Fourier Transform FFT) of these signals in each window. In some embodiments, the signal can be windowed for short periods, such as ⅙ seconds for a 6 Hz single frequency sinusoidal oscillation produced by the actuator 216. Under the uncertainty principle, a shorter period may lead to a loss of frequency resolution with a gain of time resolution. Generally a useful windowing period can correspond to an inverse of the maximum oscillation frequency used in the oscillation pressure signal to provide a short window that does not result in a loss of too much frequency resolution. In other embodiments, the window may be longer, such as 4 seconds, for example. It can be understood that the signals can be assumed to be sufficiently stationary due to the band-pass filtering, and because of the short windowing duration. In some embodiments, a Hanning-type or Hamming-type window can be used to further help enforce periodicity by reducing the signal amplitude near the window edges to reduce leakage in the frequency domain. In other embodiments, the windows can be overlapping windows (e.g. with a maximum overlap of about 50% between adjacent windows). In other embodiments, other types of windows may be appropriate for use. For example, in some cases it may be possible to use rectangular windows.

Still at act 306, after the windowing function has been applied, the Fourier transform of the pressure and flow rate in each time window may be used to obtain an estimate of the average mechanical impedance $Z_{rs}$ in that time window. More specifically the mechanical impedance can be expressed as a ratio between the Fourier transforms of the pressure and flow rate signals in each window:

$$Z_{rs}(\omega) = \frac{P(\omega)}{Q(\omega)} \quad (1)$$

where $P(\omega)$ is the FFT of the measured pressure signal and $Q(\omega)$ is the FFT of the measured flow rate signal at the angular frequency $\omega=2\pi f$ where f is the oscillation frequency used for FOT. Equation 1 can be applied to determine impedance by using pressure and flow rate measured at the airway opening of the user 210.

The mechanical impedance $Z_{rs}$ is a complex quantity with a real part corresponding to respiratory resistance ($R_{rs}$) which can be largely due to airflow resistance of intrathoracic and extrathoracic airways, lung tissue and the chest wall of the user 210 and an imaginary part corresponding to reactance ($X_{rs}$) which can arise from elastic properties of the lung and chest wall of the user 210, and the inertia of the oscillating air. The impedance can thus be described as a sum of the real and imaginary parts as shown in equation 2.

$$Z_{rs}(\omega)=R_{rs}(\omega)+jX_{rs}(\omega) \quad (2)$$

The parameters $R_{rs}(\omega)$ and $X_{rs}(\omega)$ may be characterized by fitting various respiratory models to the measured data to identify various respiratory system characteristics. For example, a commonly used model is the Single Compartment Model in which $R_{rs}(\omega)$ may be assumed to be constant with frequency $\omega$ so that $$X_{rs}(\omega) = \omega I_{rs} - \frac{E_{rs}}{\omega},$$

where $E_{rs}$ and $I_{rs}$ can be idealized lumped elements that represent the elastance and inertance of the respiratory system, respectively. Accordingly, examples of respiratory system characteristics include reactance/elastance and also inertance.

It may be also noted that the determination of the resistance and reactance in each time window yields continuous functions with respect to time, $R_{var}(t)$ and $X_{var}(t)$, for the chosen frequency of oscillation. In cases where multiple frequencies are used in the FOT oscillation signal, then the resistance and reactance may be calculated in the manner described above for each frequency separately. A separate time course behavior of the $R_{var}(t)$ and $X_{var}(t)$ may be developed for each frequency considered for analysis. Alternatively, the mean values of $X_{var}$ may be examined for different frequencies by plotting the mean values of $X_{var}$ against oscillation frequency. The same may be done for $R_{var}$. It may be noted that there may be a single band-pass filter that may be configured to sequentially filter each frequency separately or there may be multiple band-pass filters each tuned at a unique frequency from the set of oscillation frequencies that are used contemporaneously to perform filtering (e.g. a comb filter). As noted previously the volume, V(t) may be determined as the integral of the flow rate signal.

Still at act 306, the impedance that is determined according to equation (1) is repeatedly performed for an initial period of time ($t_B$), such as about 1, about 2, about 5, or about 10 seconds, for example, to obtain a baseline for the impedance $Z_{ref,w}(t)$ of the user's respiratory system that is indicative of their normal, healthy, functioning respiratory system. This may be done in different ways and one example of how to determine the baseline weighted impedance $Z_{ref,w}(t)$ is to obtain a weighted measure according to equation (2):

$$Z_{ref,w}(t)=[(R_{ref}(t)*w_R)^2+(X_{ref}(t)*w_X)^2]^{1/2} \quad (2)$$

where, $Z_{ref,w}(t)$ is the baseline weighted impedance over a monitoring time period, such as about 10 seconds for example, although other time periods can be used such as about 5 seconds, 20 seconds, and 60 seconds. When longer time periods are used, averaging can be used to reduce noise. For example, if the time used to collect data to determine the baseline measurements is about 60 seconds, then averaging can be done six times to get a baseline reading for monitoring time periods of 10 seconds. The baseline weighted impedance value is determined during an initial monitoring time period when the user first starts to use the breathing assistance device 202. The benefit of determining the baseline reading on a per user basis is the personalization aspect. For example, two patients with the same physical size (e.g. height and mass) and the same gender may still have two different breathing patterns and will therefore have different baseline weighted impedance values.

The parameters $w_R$ and $w_X$ are weights that are applied to the determined resistance and reactance, respectively, during the monitoring time interval. The weights $w_R$ and $w_X$ can be determined based on the particular user in case they have a respiratory condition, such as asthma for example. One way that the weights may be implemented is to have a table of weights for different diseases (i.e. respiratory conditions) and different levels of severity for each disease (i.e. for each respiratory condition). The weights can be determined from literature studies and then the particular weights for a given respiratory condition are used for a particular user when that particular user has the respiratory condition. Alternatively, the weights can be determined on a per-user basis by performing an initial assessment on the user.

This initial assessment for the weight parameters may be done to determine which of the resistance or the reactance is more important for the particular user and then the weights can be associated based on that determination. For example, from measurements of mean X and mean R, the user may be categorized as having a particular respiratory condition such as, but not limited to, asthma, COPD, CF or snoring (for example snoring can be detected as a respiratory failure since the snoring may be an alert of an impending airway closure). Based on the respiratory condition category, the relative weighting of R and X for the user is determined using a database or a lookup table based on data for populations that have the same respiratory condition. As an example, $R_{ref}$ may be weighted higher than $X_{ref}$ in users who are categorized as having asthma while $X_{ref}$ may be weighted higher than $R_{ref}$ in users who are categorized as having COPD. Accordingly, a larger or smaller weight can be applied to reactance relative to the weight that is applied to resistance depending on whether the user has a particular respiratory condition and a certain severity level for that particular respiratory condition.

In alternative embodiments, the baseline weighted impedance value can be redetermined at regular intervals after the initial baseline weighted impedance has been determined. For example, the baseline weighted impedance can be determined roughly about every 5 minutes, 10 minutes, 30 minutes, 60 minutes of more. The frequency used for determining revised and up to date baseline weighted impedance values may be determined based on whether the user is suffering from some type of chronic respiratory condition. For example, if the patient is suffering from severe sleep apnea, the first 5 minutes of sleep may be a good reference for the rest of the night. However, if the patient is suffering from COPD or severe asthma, the weights may be determined before the patient falls asleep and on a shorter, more regularly, e.g. about every 5 minutes. This is due to the nature of the disease and the fact that asthma and COPD are small airway disease, but sleep apnea is an upper airway disease.

It should be noted that in cases where the user 210 suffers from a chronic respiratory condition then the baseline weighted impedance value may be determined for the user 210 right after the user has undergone some treatment and their respiratory system is operating normally. The treatment may include inhaled medicine from an air puffer, taking other drugs or receiving treatment from other devices to help expand the airways, and possibly loosen and expel mucus from their lungs. Alternatively, the baseline weighted impedance value may be obtained from using standard breathing patterns that are expected for that user 210 based on standard breathing patterns for a healthy population who have comparable physiological characteristics as the user, such as weight (within +/−10%), height (within +/−10%), and gender. Alternatively, the baseline weighted impedance value may be obtained by using the standard breathing patterns and also performing some measurements after the user 210 has received treatment.

The method 300 then proceeds to act 310 where feature extraction is performed. At this point, the breathing signature classifier 229c can obtain values for input features for the breathing signature machine learning model. These input feature values may be obtained from measured and/or calculated parameters. For example, in at least one embodiment the input feature values may be determined from measured air pressure and/or measured air flow rate. Alternatively, in at least one embodiment the input feature values may be determined from the calculated airway impedance that is determined using one or multi-frequency FOT. Alternatively, in at least one embodiment the input feature values may be determined from: (1) measured air pressure, (2) measured air flow rate; and/or (3) calculated airway impedance determined using one or multi-frequency FOT. When using one or multi-frequency FOT, classification can be made using resistance (R) and reactance (X) resulting from the FOT measurements at different oscillation frequencies. The oscillation frequency can be anywhere between about 0.01 Hz to about 100 MHz and the R and X measured at different frequencies can be used together to classify the patient breathing signature. It should be noted that if impedance, reactance and/or resistance is not used in feature extraction then the performance of the FOT method may not be needed, act 302 does not have to be performed and the air pressure and airflow rate can be measured while the patient is simply breathing without being provided with any perturbation signals. This can also apply for acts 310 performed for methods 350 and 400.

Figure 4E:
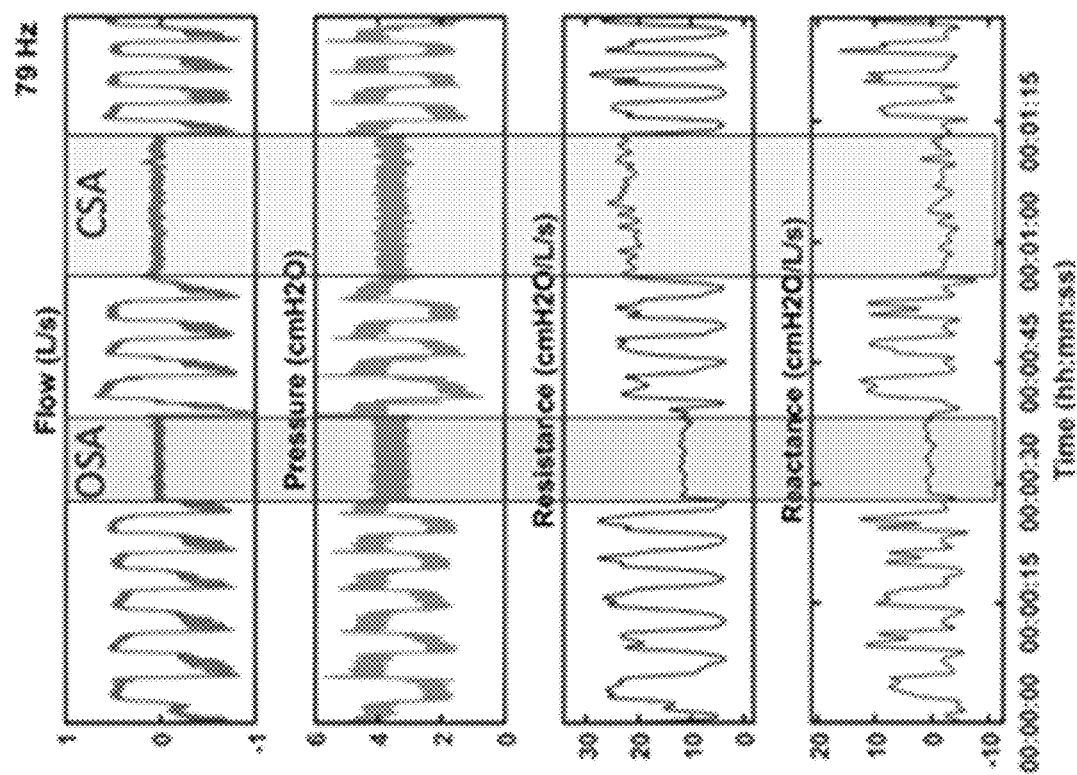
FIGS. 4B to 4E are plots of measurements of air flow and air pressure and calculations of resistance and reactance in real time for different FOTs at frequencies of 4 Hz, 17 Hz, 43 Hz and 79 Hz, respectively.
Figure 4D:
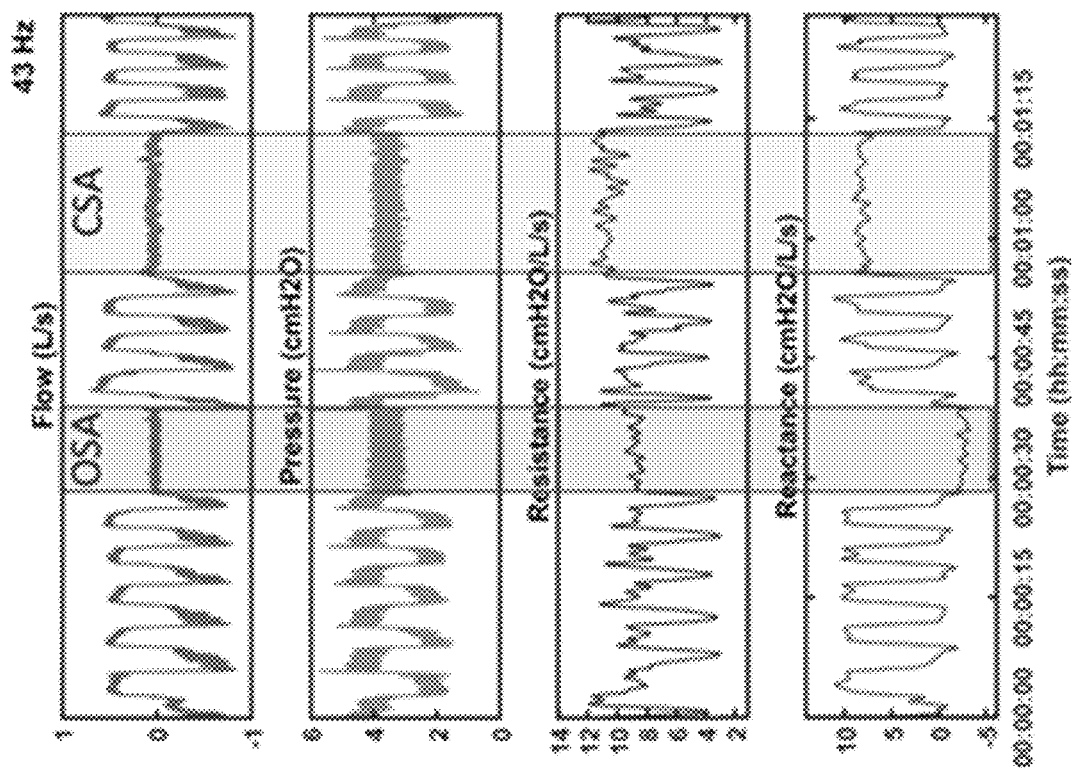
Figure 4C:
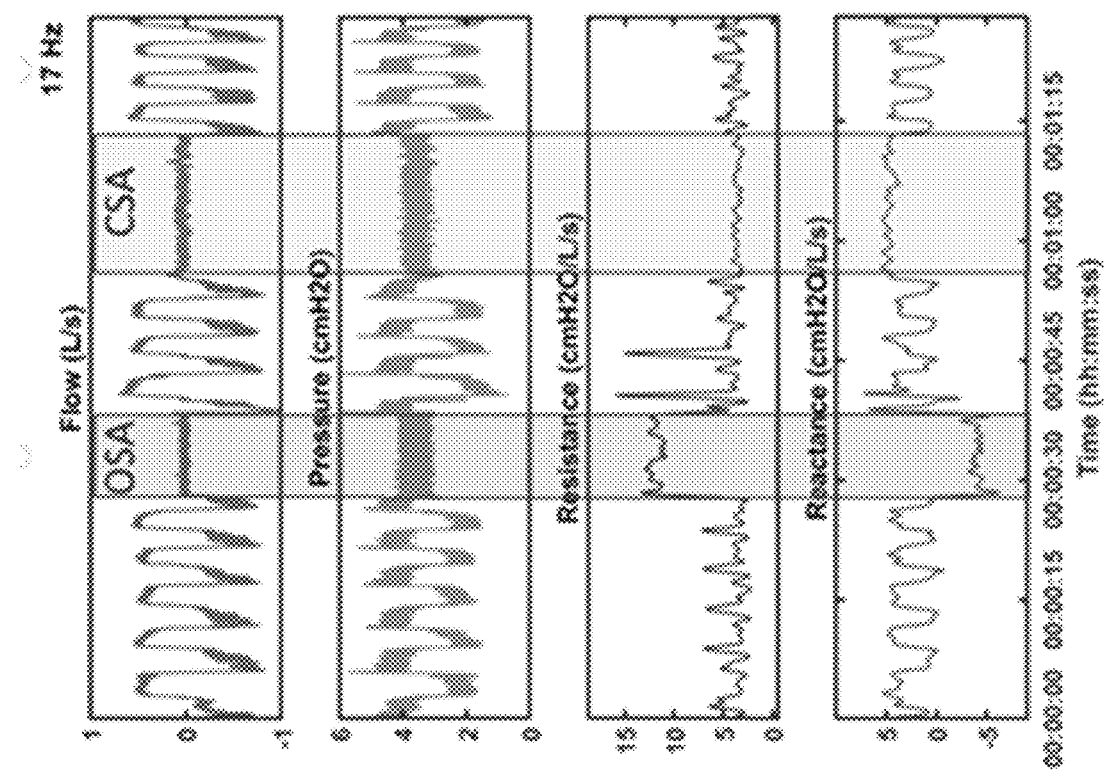
Figure 4B:
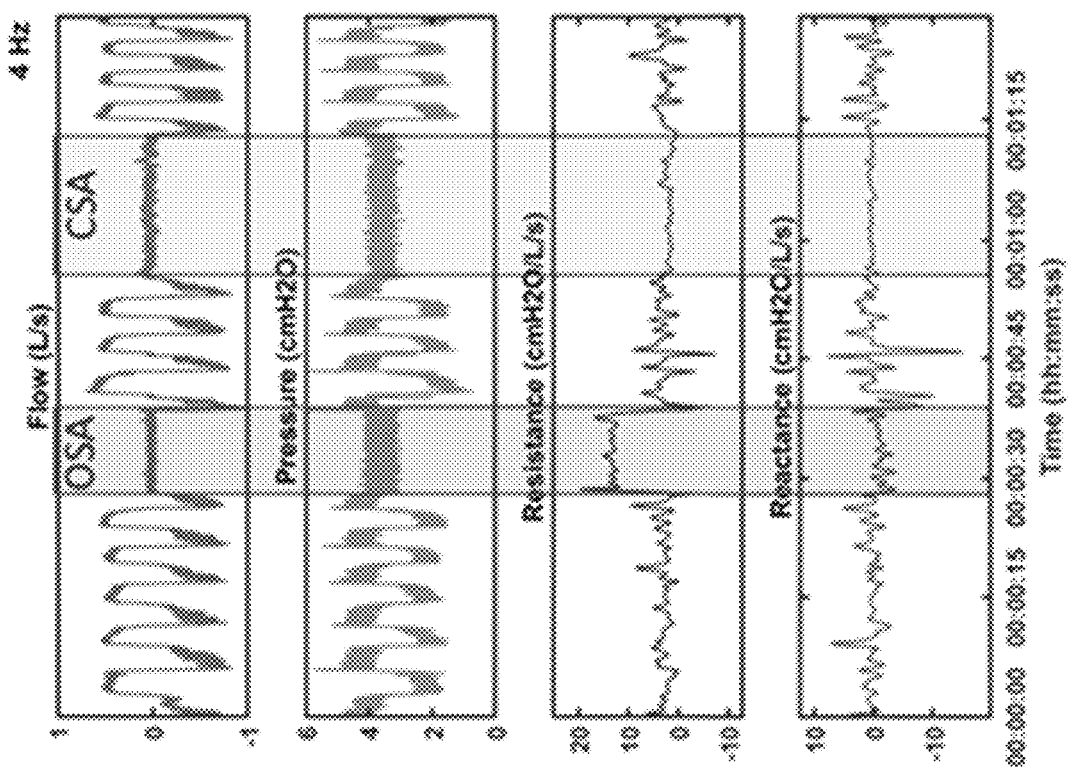

For example, referring now to FIGS. 4B-4E, shown therein are plots of measurements of air flow and air pressure and calculations of resistance and reactance in real time for different FOTs at frequencies of 4 Hz, 17 Hz, 43 Hz and 79 Hz, respectively, from a representative patient. The measured data shows events where the patient had Obstructive Sleep Apnea (OSA) and Central Sleep Apnea (CSA). It can be seen in FIG. 4B that during an OSA event the FOT determined R at 4 Hz increases while during a CSA event, the FOT determined R at 4 Hz does not increase. In FIG. 4C it can be seen that during an OSA, the FOT determined R at 17 Hz increases while during a CSA event, the FOT determined R at 17 Hz does not increase. FOT determined Reactance, X, at 17 Hz however decreases during an OSA and increases during a CSA. In FIG. 4D it can be seen that during an OSA, the FOT determined Reactance, X, at 43 Hz decreases during an OSA and increases during a CSA. In FIG. 4E it can be seen that during an OSA, the FOT determined Resistance, R, at 79 Hz remains at the mean during an OSA and increases during a CSA.

The features that may be used to obtain input feature values from these measured or calculated values may be at least one of the features that were described previously when the machine learning models 229f were discussed. Preferably, the input feature can be the PSD of the measured air pressure, the PSD or the measured airflow rate and/or the PSD of the calculated airway impedance depending on the embodiment that is used.

At act 312, the breathing signature machine learning model is applied to the extracted input feature values to determine the breathing signature. In one example embodiment, the breathing signature machine learning model may be a random forest classifier having 200 trees and the input feature that was used was the PSD of the air flow rate measured while obtaining FOT baseline data. For example, the breathing signature machine learning model may, in at least one embodiment, use a Random Forest model in which different trees are used to distinguish breathing pattern features of the patient with previous nights of using the breathing assistance device and will classify at an accuracy higher than 90% whether this is the same patient or not. For example, in at least one other example embodiment, specific features may be found to have a higher weight than for other patients, and therefore the model will be trained further for the specific patient which will be unique to that patient. In at least one alternative embodiment, a deep learning model can be used as well.

Testing was done to determine if there is a detectable difference among the PSD of patient baseline FOT flow data using the machine learning model and input feature values described in act 312 on a data set containing 5 different samples of baseline airflow data, (e.g. normal breathing) that was 60 seconds in length (with a 200 Hz sampling rate), for each of three patients (depicted by the circle, diamond and triangle markers) for a total of 15 samples. Each sample was normalized such that it's maximum value was equal to 1 and the PSD was calculated for each sample using Welch's method. The samples were vertically stacked to form a data matrix containing samples as the rows and PSD as the columns. As per convention, this data matrix was column-mean centered before PCA and PPA were applied as described below.

Referring now to FIGS. 4F and 4G, shown therein are the analysis of the test results using the first two scores obtained from applying Principal Component Analysis (PCA) and Projection Pursuit Analysis (PPA), respectively, when applied to the output of the breathing signature machine learning model described for step 312. The PCA was implemented using Singular Value Decomposition and the PPA was implemented using the quasi-power algorithm. PCA analysis uses the variance in data to explore high-dimensional data but PPA searches for interesting projections by optimizing kurtosis. Both FIGS. 4F and 4G show distinct clusters corresponding to the different patients that were tested. It is important to note here that the test results are unsupervised and are displaying natural relationships between the samples in this case as the model is not trained at all and there is no overfitting. PCA was used as an exploratory method to determine if breathing of different patients can be classified in different clusters and the results in the figures clearly show this. Larger datasets and supervised learning models may be used to more accurately differentiate patients based on monitoring of breathing (e.g. measured pressure and airflow rate) and the calculated airway impedance.

Referring now to FIG. 4H, shown therein is a plot of the accuracy of a patient breathing signature classifier versus the number of training days over which this classifier was trained. The data was obtained by taking 400-900 baseline samples per day from 18 patients. The input features for the patient breathing signature classifier was measured air flow rate and/or pressure. This classifier was based on a CNN using the same topology as was used for the machine learning model used for prediction of prediction of sleep disruption severity but with different parameter values used based on the training that was done.

At act 314, the method 300 involves performing breath signature classification. For example, for a given breathing assistance device, there may be a user who is designated to use that device. This user's breathing signature can be stored in the memory unit 229. When a user begins to use the breathing assistance device, the current patient breathing signature may be determined as described above. At act 316, the current patient breathing signature may then be compared to the stored patient breathing signature to determine whether the proper user is using the breathing assistance device.

If it is determined at act 316, that the current patient breathing signature is the same as the stored patient breathing signature then the method 300 can proceed to act 318 and the breathing assistance device can be used normally. However, if it is determined at act 316, that the current patient breathing signature is not the same as the stored patient breathing signature then the method 300 can proceed to act 320 where the processor of the breathing assistance device may emit a value for the control signal 212 to shut down the breathing assistance device and may optionally sound an alarm or may optionally send a report that that the current user of the breathing assistance device is not the intended patient.

Figure 5:
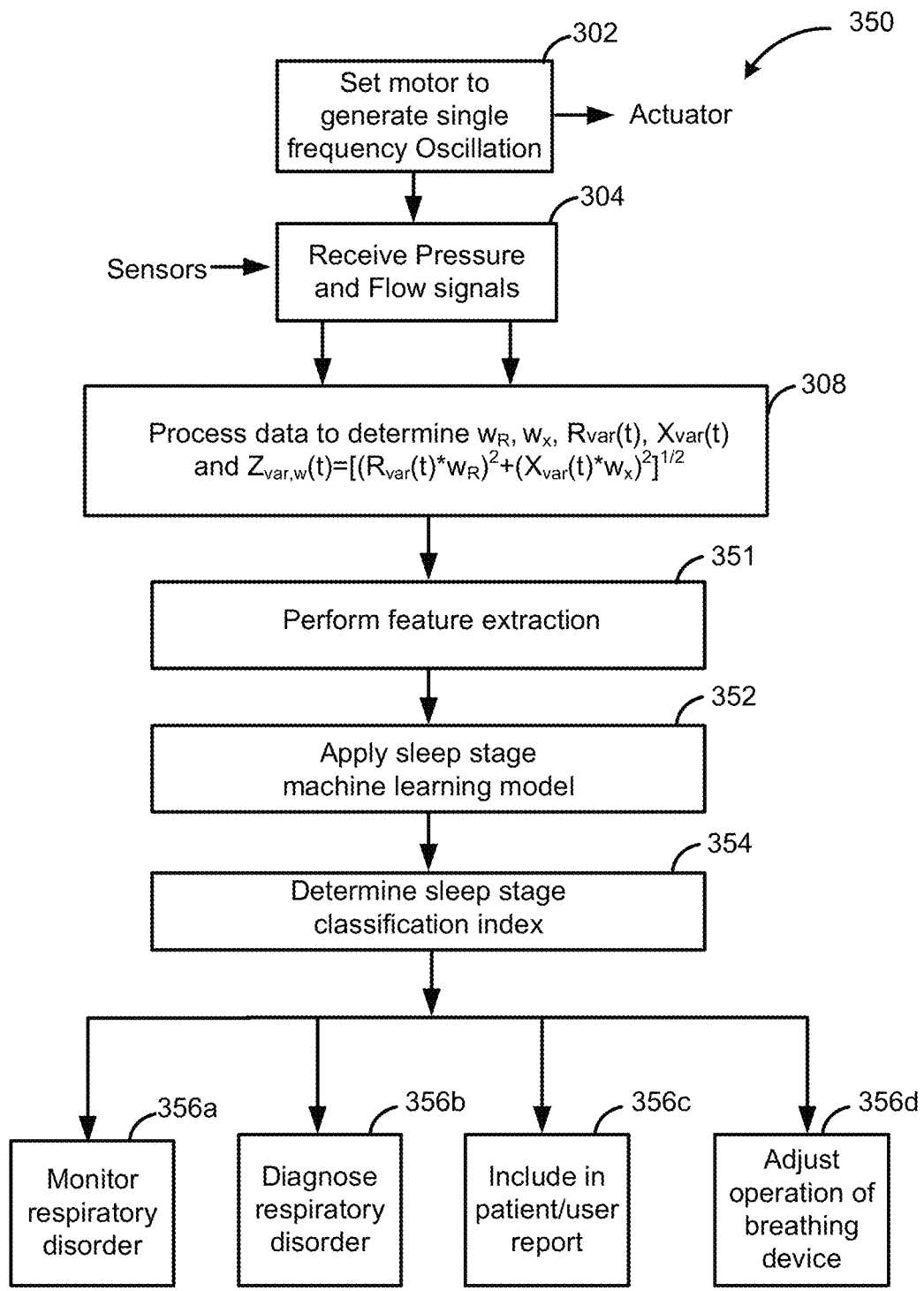
FIG. 5 is a flowchart of an example embodiment of a breathing assistance control method that utilizes patient sleep stage determination to adjust the settings of a breathing assistance device in accordance with the teachings herein.

Referring now to FIG. 5, shown therein is a flowchart of an example embodiment of a breathing assistance control method 350 that utilizes patient sleep stage determination to adjust the settings of a breathing assistance device in accordance with the teachings herein. In particular, method 350 employs machine learning to accurately determine sleep stages based of measurements of subject breathing (e.g. pressure and flow) and/or measurements of airway impedance using FOT. For example, method 350 may be used to determine various sleep stages such as awake, sleep stages 1-4, and REM (Rapid Eye Movement) sleep. In order to perform the sleep stage classification, sleep stage models are developed using standard EEG (Electroencephalography) measurements and then these results are correlated to actual measured air pressure, airflow rate, and airway impedance measurements using FOT to determine the sleep stage machine learning model. For example, other than the rate of breathing that varies at different sleep stages, the inventors have determined that there are other hidden features in airflow, pressure, R and X that can be used to determine sleep stages. For ease of explanation, the elements depicted in the breathing assistance system 200 shall be used in describing the various steps of the method 350. For example, the method 350 may be implemented by the processor 228 of the breathing assistance system 200. However, it should be understood that this technique can be used on the integrated breathing assistance device controller 250 or another applicable device.

The method 350 has many acts in common with method 300 including acts 302, and 304. It should be noted that act 306 is not needed here as the baseline reference impedance value does not need to be used but act 308 is performed in order to determine the variable reference impedance in real time.

At act 308 continuous monitoring of the weighted impedance $Z_{var,w}(t)$ is performed while the method 350 is being implemented by the breathing assistance device 202. In particular at act 308, the current weighted impedance $Z_{var,w}(t)$ for the current monitoring time period is determined according to equation (3):

$$Z_{var,w}(t)=[(R_{var}(t)*w_R)^2+(X_{var}(t)*w_X)^2]^{1/2} \quad (3)$$

It can be seen that equation (3) is similar to equation (2) in that the same weights are applied but this is done for the $R_{var}(t)$ and $X_{var}(t)$ for the current time period. It should be noted that the weights $w_R$ and $w_X$ can be different in the determination of breathing signature versus prediction of apnea.

However, the feature value extraction that is performed for method 350 at act 401 may be different than that performed in method 300 since different measurements and different features may be used by the sleep stage classification machine learning model of method 350. For example, in at least one embodiment the input feature values may be determined from at least one of measured air pressure and measured air flow rate. Alternatively, in at least one embodiment the input feature values may be determined from the calculated airway impedance that is determined using one or multi-frequency FOT. Alternatively, in at least one embodiment, the input feature values may be determined from other PSG data, such as EEG data. For example, the EEG signal may be used to label the data into different sleep stages (i.e. classes), and then the measured air pressure, airflow rate, and reactance and resistance from FOT can be used for classification. Alternatively, in at least one embodiment the input feature values may be determined from combinations of: (1) (a) measured air pressure and/or (b) measured air flow rate; (2) using calculated airway impedance determined using one or multi-frequency FOT; and (3) using other PSG data, such as EEG data as described above. When using one or multi-frequency FOT, classification can be made using resistance (R) and reactance (X) resulting from the FOT measurements at different oscillation frequencies. The oscillation frequency can be anywhere between about 0.01 Hz to about 100 MHz and the R and X measured at different frequencies can be used together to classify the patient breathing signature.

At act 352, the method 300 involves applying the sleep stage machine learning model to determine the patient's current sleep stage which might be awake, sleep stages 1-4, and REM (Rapid Eye Movement) sleep. The sleep stage machine learning model may be implemented using Random forest, a logistic linear model, the K-Nearest Neighbors algorithm, the Feature-Based Dissimilarity Space Classifier (FDSC), neural networks including a CNN or a Re-current Neural Network (RNN), support vector machines or deep learning. At act 354, the output of the sleep stage machine learning model is used to determine a sleep stage classification index (Kss) that varies from 0 to 5 by assigning 0 to the stage awake, assigning 1 to sleep stage 1, assigning 2 to sleep stage 2, assigning 3 to sleep stage 3, assigning 4 to sleep stage 4, and assigning 5 to the REM stage.

Various actions may then be performed after the sleep stage classification index is determined. For example, in at least one embodiment, at act 356a, the sleep stage classification result can be stored along with measured respiratory data to monitor how a respiratory disorder may affect breathing based on the sleep stage of the patient. Alternatively, in at least one embodiment, at act 356b, the sleep stage classification result can be used along with measured respiratory data to diagnose a respiratory disorder. Alternatively, in at least one embodiment, at act 356c, the sleep stage classification result can be recorded in a report for a patient or a user of the breathing assistance device.

Alternatively, in at least one embodiment, at act 356d, the sleep stage classification index may be incorporated into the intervention/prevention of respiratory failure. For example, the sleep stage classification index (Kss) can be used in one of methods 450, 500 or 600. As another example, if it is determined that a patient is in the REM sleep stage, then OSA events are at their worst, the confidence that the prediction algorithm predicting a respiratory failure (e.g. methods 500 or 600) increases, and an intervention may be more confidently be applied (e.g. an increase in pressure provided by the breathing assistance device to prevent an apnea event from occurring). Alternatively, if it is determined that the patient is in sleep stage 1, and a prediction of a respiratory failure has occurred, then this is likely is a false positive since in sleep stage 1 is it unlikely that a respiratory failure event like a sleep apnea will occur.

It should be noted that any one, two or three of acts 356a to 356d may be optional in some embodiments.

Figure 6A:
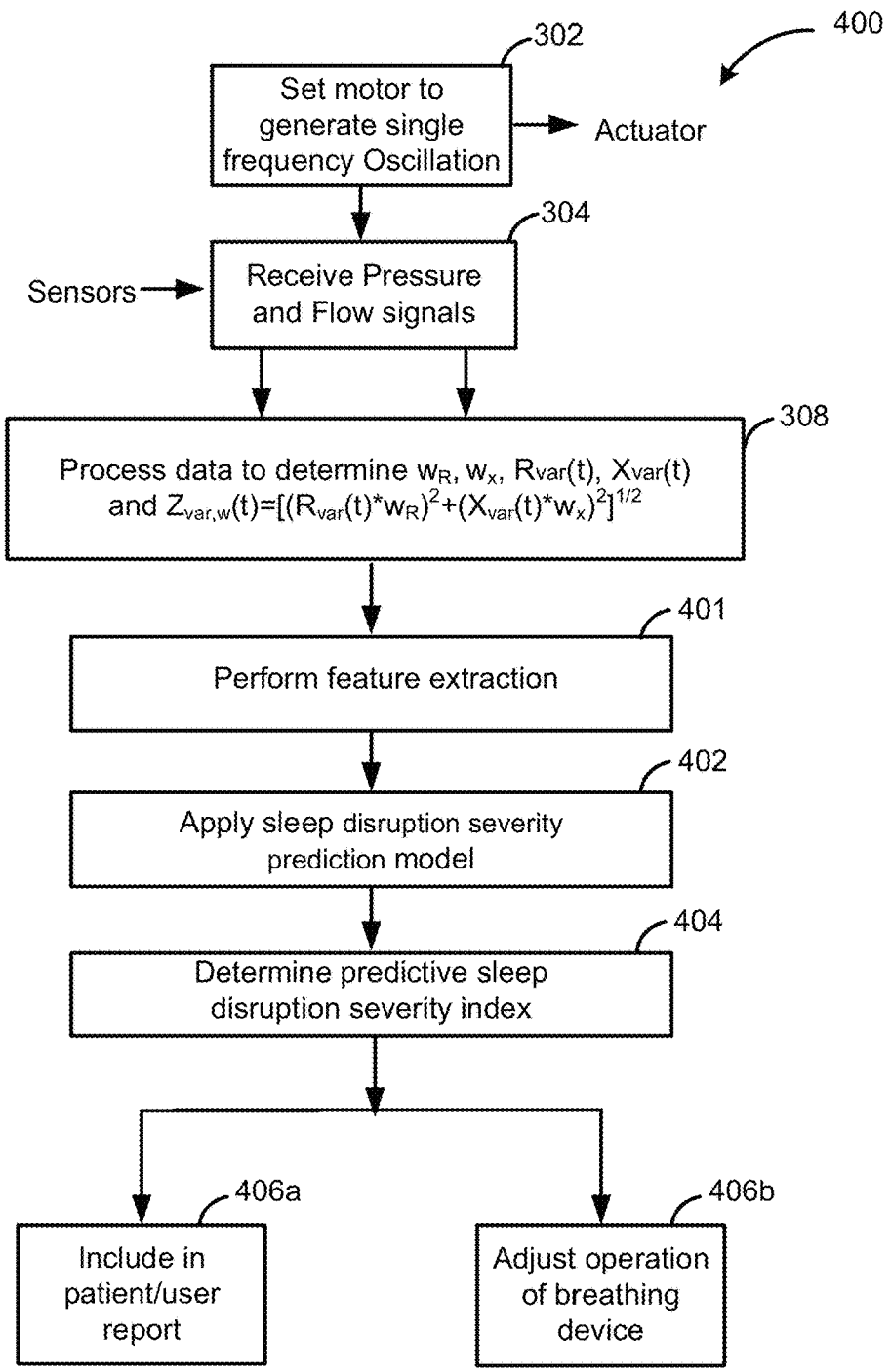
FIG. 6A is a flowchart of an example embodiment of a breathing assistance control method that utilizes prediction of sleep disruption severity to adjust the settings of a breathing assistance device in accordance with the teachings herein.

Referring now to FIG. 6A, shown therein is a flowchart of an example embodiment of a breathing assistance control method 400 that utilizes prediction of sleep disruption severity to adjust the settings of a breathing assistance device in accordance with the teachings herein. In particular, method 400 employs machine learning to predict sleep disruption severity based of measurements of subject breathing (e.g. pressure and flow) and/or measurements of airway impedance using FOT.

For example, method 400 can employ machine learning to build a real-time prediction model of severity of airway obstruction events based on measurements of subject breathing (e.g. pressure and flow) and/or measurements of airway impedance using FOT. The determined airway impedance (using FOT) may be used to improve differentiation of obstructive and central sleep apnea events. Obstructive apnea is due to a blockage in the airway and an increase of pressure can prevent or remove it. Central apnea is when the effort to breathe is absent and there is no airway blockage. When used in positive airway pressure (PAP) machines, the prediction ability for the sleep disruption severity machine learning model to differentiate between obstructive and central sleep apneas can be used to determine whether the control signal is generated to control the breathing assistance device 202 to intervene and remove the obstruction or whether the PAP settings should be kept as is. Furthermore, power-spectral density calculations of the airway impedance may be used to improve accuracy of the predictive sleep disruption severity machine learning model.

For ease of explanation, the elements depicted in the breathing assistance system 200 shall be used in describing the various steps of the method 350. For example, the method 400 may be implemented by the processor 228 of the breathing assistance system 200. However, it should be understood that this technique can be used on the integrated breathing assistance device controller 250 or another applicable device.

The method 400 has many acts in common with method 350 including acts 302, 304, and 308. As with method 350, it should be noted that for method 400 act 306 is not needed here as the baseline reference impedance value does not need to be used but act 308 is performed in order to determine the variable reference impedance in real time.

However, the feature value extraction that is performed for method 400 at act 401 may be different than that performed in method 300 or method 350 since different measurements and different features may be used by the predictive sleep disruption severity machine learning model of method 400. For example, in at least one embodiment the input feature values may be determined from measured air pressure and/or measured air flow rate. Alternatively, in at least one embodiment the input feature values may be determined from the calculated airway impedance that is determined using one or multi-frequency FOT. Alternatively, in at least one embodiment the input feature values may be determined from combinations of: (1) (a) measured air pressure and/or (b) measured air flow rate; and (2) using calculated airway impedance determined using one or multi-frequency FOT. When using one or multi-frequency FOT, classification can be made using resistance (R) and reactance (X) resulting from the FOT measurements at different oscillation frequencies. The oscillation frequency can be anywhere between about 0.01 Hz to about 100 MHz and the R and X measured at different frequencies can be used together to classify the patient breathing signature.

At act 402, the method 400 involves applying the predictive sleep disruption severity machine learning model to predict the severity of an upcoming sleep disruption event such as an obstructive sleep apnea or a central sleep apnea. This includes differentiation of the duration of these events. In at least one embodiment, the accuracy of the predictive sleep disruption severity machine learning model may be improved by taking a base model and adding per-patient individualization. For example, the base model may be a model that is trained on a general population. In other places the base model may be base breathing which is healthy breathing. When a specific patient starts using a breathing assistance device that uses machine learning models for breathing signature classification, based on a generalized model a breathing signature with an accuracy of, for example 90%, may be formed. However, as the patient keeps using this device the breathing signature classification machine learning model learns and adjusts features that are used for that specific patient which will increase the accuracy of the patient breathing signature classification to close to 100%. This applies to predictions, severity and sleep stages as well. These additions may be done while measuring a few nights of data from a specific patient.

At act 404, the output of the predictive sleep disruption severity machine learning model is used to determine a predictive sleep disruption severity index (Ksd) that varies from 0 to 1 or may be indicated as being a class #. For example, for the index varying from 0 to 1, the sleep disruption severity machine learning model may output 1 of N different classes of sleep disruption severity with class 1 having the lowest severity and class N having the highest severity where N is an integer. The predictive sleep disruption severity index can then be determined by dividing the class number provided by the predictive sleep disruption severity machine learning model by N. Alternatively, the predictive sleep disruption severity index may be the class #itself.

Various actions may then be performed after the predictive sleep disruption severity index is determined. For example, in at least one embodiment, at act 406a, the predictive sleep disruption severity index can be recorded in a report for a patient or a user of the breathing assistance device 202. Alternatively, in at least one embodiment, at act 406b, the predictive sleep disruption severity index may be incorporated into the intervention/prevention of respiratory failure to adjust the operation of the breathing assistance device 202. For example, the predictive sleep disruption severity index (Ksd) can be used in one of methods 450, 500 or 600. For example, one of methods 500 or 600 may predict that a sleep apnea will soon occur and the predictive sleep disruption severity index can be used to determine how much to increase pressure to prevent the sleep apnea event from occurring. So if the sleep disruption severity index is at a low value (e.g. a severity class 1) then the PAP pressure may only need to be raised by 0.5 cmH2O. However, if the sleep disruption severity index is at a slightly higher level (e.g. a severity class 2), then the PAP pressure will have to be increased by a greater amount such as increasing the pressure by 1 cm H2O, for example, and so on and so forth.

Figure 6B:
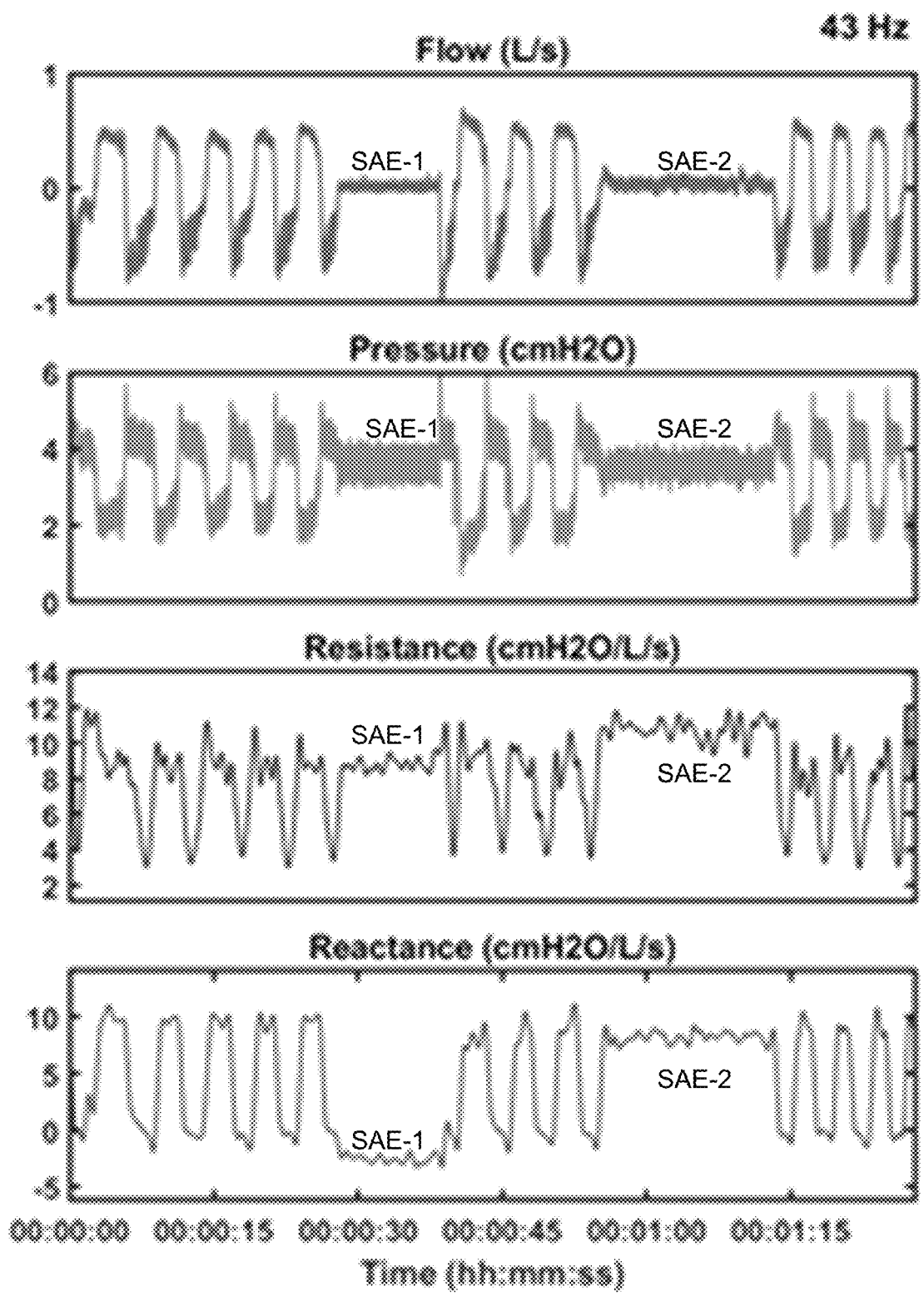
FIG. 6B is a plot of flow, pressure, resistance and reactance signals measured for a patient showing examples of two sleep apnea events of different classes.

Alternatively, another way to determine the predicted sleep disruption severity index is based on the length of the predicted apnea event. For example, in the case of sleep apnea, the predictive sleep disruption severity index for a sleep apnea can be classified in a manner such as the following: Class1: the sleep apnea lasts less than 5 seconds; Class2: the sleep apnea lasts between 5 and 10 seconds; Class 3: the sleep apnea lasts between about 10 to 15 seconds and Class 4: the sleep apnea event lasts longer than 15 seconds. For instance, referring now to FIG. 6B, shown therein is a plot of flow, pressure, resistance and reactance signals measured for a patient showing examples of two sleep apnea events of different classes in which the first sleep apnea event (SAE-1) is a class 2 and the second apnea event (SAE-2) is a class 4.

As another example, in the case of other respiratory failures for other respiratory diseases, the definition of the predicted sleep disruption severity index intensity can change. For example, in COPD the predicted sleep disruption severity index can represent how severe the expiratory flow limitation (EFL) is which may be determined from how fast the expiration flow plateaus. This may also be extracted from the measured R and X using the FOT method.

Figure 6C:
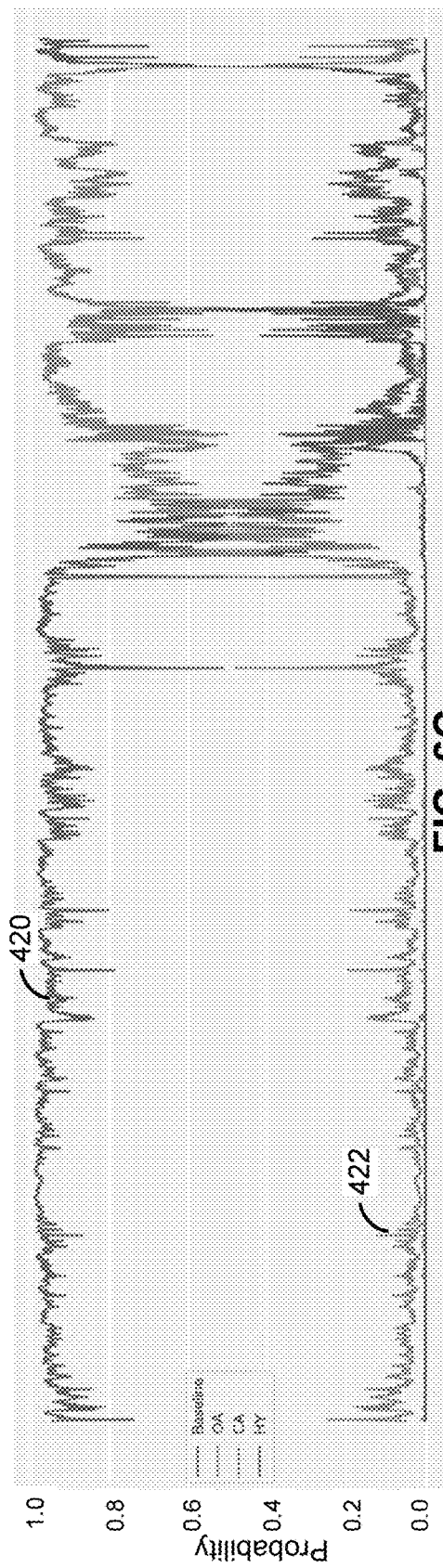
FIG. 6C shows predicted signals determined prior to and during an example obstructive apnea event experienced by an actual patient.

Referring now to FIG. 6C shown therein are predicted signals determined prior to and during an example obstructive apnea event experienced by an actual patient. The curve 420 representing the probability of predicted normal breathing is close to 1 in the beginning while the curve 422 representing the probability of an obstructive apnea is near zero. At some point (a probability of 0.5 in this case) the curves for these two probabilities cross over and an obstructive apnea is predicted.

Figure 6D:
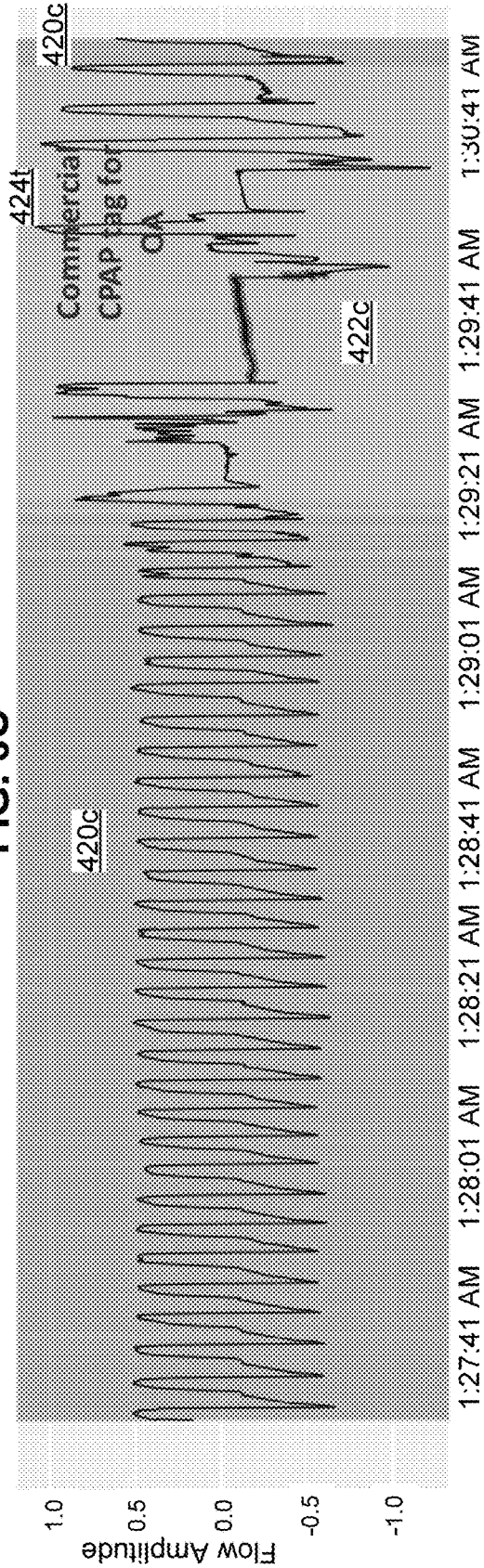
FIG. 6D shows the actual breathing measurements that correspond to the predicted signals of FIG. 6C prior to and during the example obstructive apnea event experienced by the patient.

Referring now to FIG. 6D, shown therein are the actual breathing measurements that correspond to the predicted signals of FIG. 6C prior to and during the example obstructive apnea event experienced by the patient. The flow rate of breathing is shown for the patient using a background color that corresponds to the curves for the probabilities in FIG. 6C. Therefore, the background color 420c represents normal breathing while the background color 422c represents breathing associated with an obstructive apnea event. It can be seen that very early in when the background color changes from blue (420c) to orange (422c) this reflects that the probability of an obstructive apnea has increased. It is also shown that in a normal commercial CPAP machine that this specific patient was using, the obstructive apnea was tagged 424t (detected) 20-30 seconds after the prediction of the obstructive apnea event was made using the techniques described in accordance with the teachings herein.

Figure 6E:
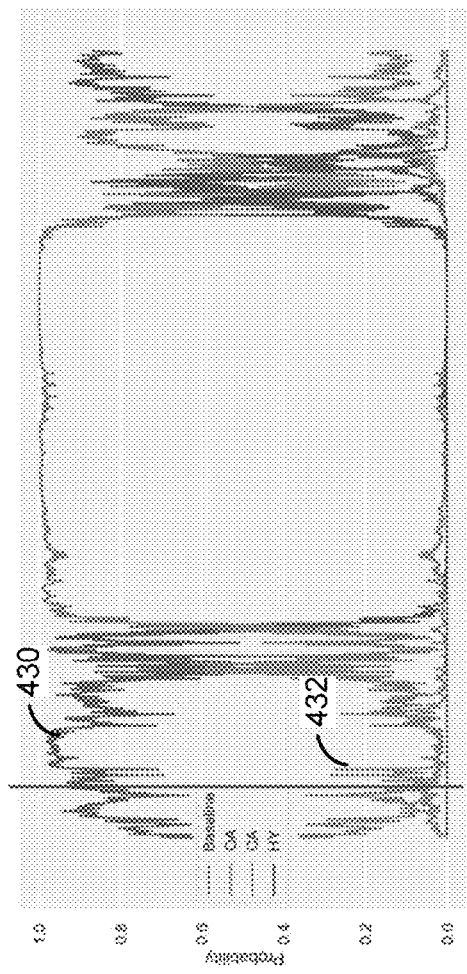
FIG. 6E shows predicted signals determined prior to and during an example central apnea event experienced by an actual patient.

Referring now to FIG. 6E, shown therein are predicted signals determined prior to and during an example central apnea event experienced by an actual patient. The curve 430 representing the probability of predicted normal breathing (in blue) is close to 1 in the beginning while the curve 432 representing the probability of a central apnea (in green) is near zero. At some point (a probability of 0.5 in this case) these two probabilities cross over and a central apnea is predicted.

Figure 6F:
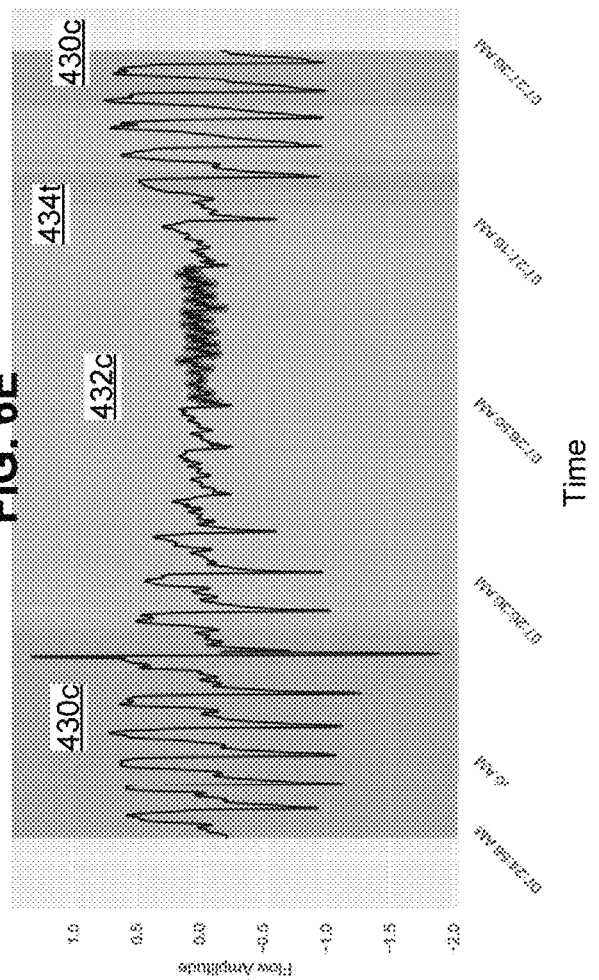
FIG. 6F shows the actual breathing measurements that correspond to the predicted signals of FIG. 6E prior to and during the example central apnea event experienced by the patient.

Referring now to FIG. 6F, shown therein are the actual breathing measurements that correspond to the predicted signals of FIG. 6E prior to and during the example central apnea event experienced by the patient. The flow rate of breathing is shown for the patient with background color that corresponds to the curves for the probabilities in FIG. 6E. Therefore, the background color 430c represents normal breathing while the background color 432c represents breathing associated with an central apnea event. It can be seen that very early in the when the background color changes from blue (430c) to green (432c) reflecting that the probability of a central apnea has increased. It is also shown that in a conventional commercial CPAP machine that this specific patient was using, the central apnea was tagged 434t (detected) 30-40 seconds after our prediction of the obstructive apnea event was made using the techniques described in accordance with the teachings herein.

Figure 7:
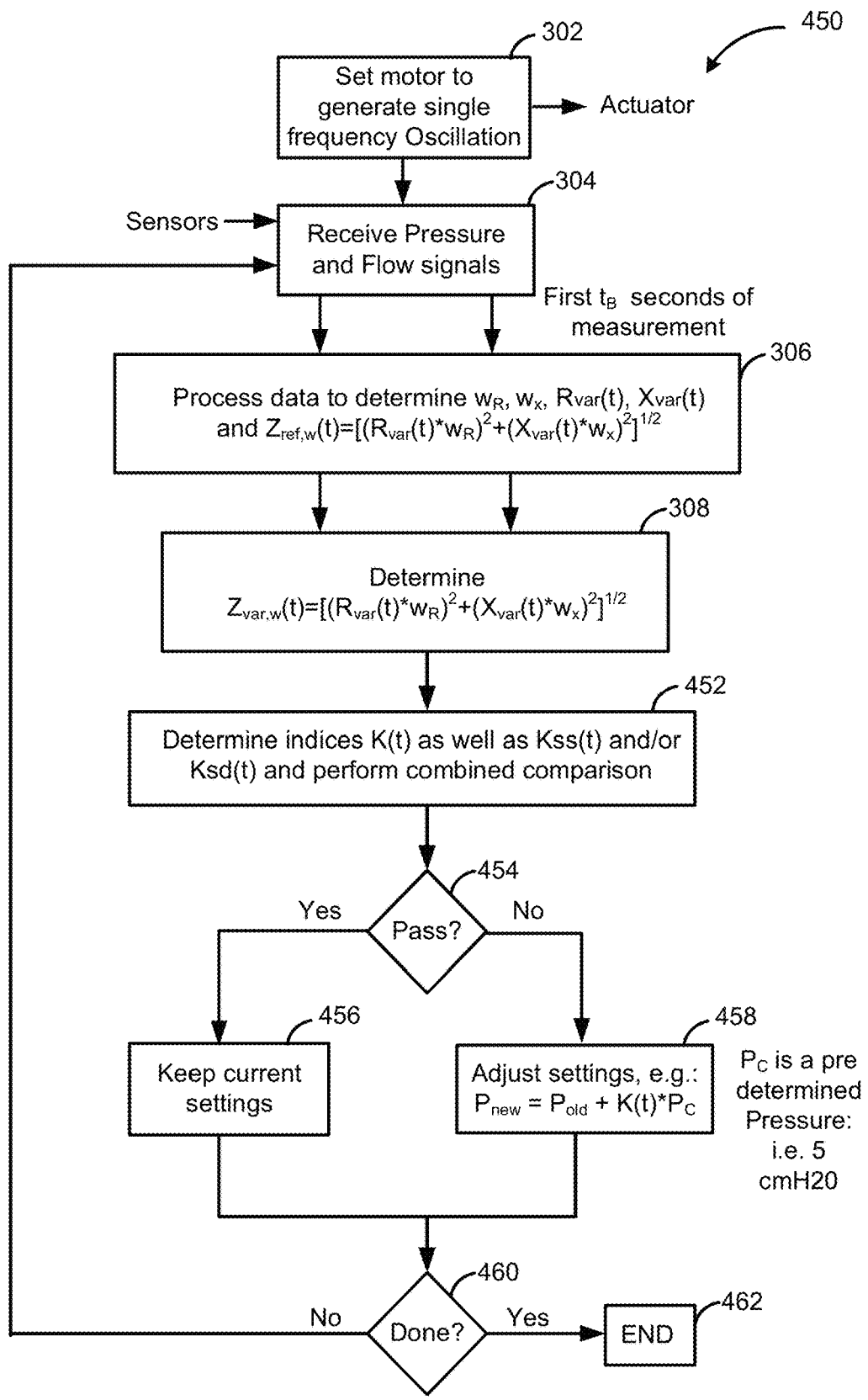
FIG. 7 is a flowchart of an example embodiment of a breathing assistance control method that utilizes respiratory failure detection and at least one of a sleep stage classification index and a predicted sleep disruption severity index to adjust the settings of a breathing assistance device in accordance with the teachings herein.

Referring now to FIG. 7, shown therein is an example embodiment of a breathing assistance control method 450 that utilizes respiratory failure detection and at least one of a sleep stage classification index and a predicted sleep disruption severity index to adjust the settings of a breathing assistance device in accordance with the teachings herein. For ease of explanation, the elements depicted in the breathing assistance system 200 shall be used in describing the various steps of the method 450. For example, the method 450 may be implemented by the processor 228 of the breathing assistance system 200. However, it should be understood that this technique can be used on the integrated breathing assistance device controller 250 or another applicable device.

The method 450 incorporates acts 302 to 308 which have been explained previously. At act 452, the method 450 determines the value for a time varying respiratory index K(t) (i.e. a respiratory index signal) based on a combination of the baseline weighted impedance $Z_{ref,w}(t)$ and the current weighted impedance $Z_{var,w}(t)$. For example, the time varying respiratory index K(t) can be determined based on a deviation of the current weighted impedance $Z_{var,w}(t)$ relative to the baseline weighted impedance $Z_{ref,w}(t)$, an example of which is shown in equation 4:

$$K(t) = SSE(Z_{var,w(t)} \text{ and } z_{ref,w(t)}) = \frac{\sum (Zvar, w(t) - Zref, w(t))^2}{\sum (Zref, w(t))^2} \quad (4)$$

so that the respiratory index signal K(t) is normalized to 1. It should be noted that the above method for determining the value of the index K(t) is provided as an example and that in alternative embodiments the index K(t) may be determined using other methods. For example, the index K(t) may be determined using the normalized summed standard deviation of $Z_{var,w}(t)$ relative to $Z_{ref,w}(t)$. Alternatively, other statistical methods may be applied to determine/track changes in $Z_{var,w}(t)$ relative to $Z_{ref,w}(t)$.

Act 452 also includes determining the sleep stage classification index over time (i.e. Kss(t)) and/or the predicted sleep disruption severity index over time (i.e. Ksd(t)). The method 450 then combines these indices. This combination can be done by comparing each index to its own respective threshold, which can be obtained from a table of thresholds that are defined for detecting respiratory failure conditions using these respective indices based on experimental or population data, and coming up with an overall threshold comparison confirmation to obtain a result with increased confidence by including Kss(t) and/or Ksd(t).

It should be noted that each index signal K(t), Kss(t) and Ksd(t), while having a time dependency are actually values for discrete time points where each time point corresponds to a particular monitoring time period depending on the window size and overlap of windows.

For example, K(t) can be compared with a threshold Th and if there is a pass then Kss(t) can be compared to its sleep stage threshold and/or Ksd(t) can be compared to its own sleep disruption severity threshold to confirm that the comparison of K(t) with its threshold was a valid pass. Alternatively, all three indices may be combined according to a mathematical mapping function and then compared to an index which has been determined based on a table of thresholds that are defined for detecting each respiratory failure condition based on experimental or population data while performing the same mathematical mapping. For example, the mathematical mapping may be K,ss(t)=K(t)*Kss(t) or K,sd(t)=K(t)*Ksd(t) or K,ss,sd(t)=K(t)*Kss(t)*Ksd(t). Alternatively, instead of combining through multiplication the combination can be through a weighted sum such as K,ss(t)=K(t)/(K(t)+Kss(t))+Kss(t)/(K(t)+Kss(t)), as an example, or by an average such as K,ss(t)=(K(t)+Kss(t))/2. Alternatively, another mathematical mapping function may be used.

Accordingly, the combined index is used to detect (or predict as in method 500 or 600) respiratory failure and may be used to tailor the treatment (i.e. adjust the settings of the breathing assistance device according to the user's needs). For example, if comparison of the combined index with one or more thresholds indicates a pass then this indicates that the user 210 is not experiencing any respiratory failure or that there are no significant changes in the user's respiratory health. In this case the method 450 proceeds to act 456 where the current settings for the breathing assistance device 202 are maintained.

However, if the comparison for the combined index indicates a respiratory failure is occurring or that a respiratory failure is predicted to occur then the user 210 may be experiencing respiratory failure or there has been some other significant change in their respiratory health during the current monitoring time period. In this case, the method 450 proceeds to act 458 where the settings for the breathing assistance device 202 are changed so that the user's respiratory health improves and they no longer experience the respiratory failure they were previously experiencing. The adjustments may be made in various ways. The actual way of adjusting the operation of the breathing assistance device 202 may depend on the user's baseline respiratory health. The amount of the adjustment may also be based on the value of the predictive sleep disruptive severity index. The amount of adjustment may also be determined based on testing results obtained from experimental data on actual user data which are used to create adjustment factors that can be accessed in a look-up table. Furthermore previous data obtained from the patient (for example data collected from the user's previous PAP machine) can be used to adjust parameters.

After the method 450 has performed act 456 or 458, the method 450 proceeds to act 460 where it is determined whether the method 450 should keep operating. If the condition at act 460 is true then the method 450 proceeds to act 462 and ends. If the condition at act 460 is not true then the method 450 goes to act 304 and continues to obtain sensor values, monitors the current weighted impedance, generates the index values and compare them to one or more threshold values to determine when the user 210 is experiencing or is predicted to imminently experience a respiratory failure and if so, to update the operation of the breathing assistance device 202 to reduce or stop the respiratory failure.

Figure 8:
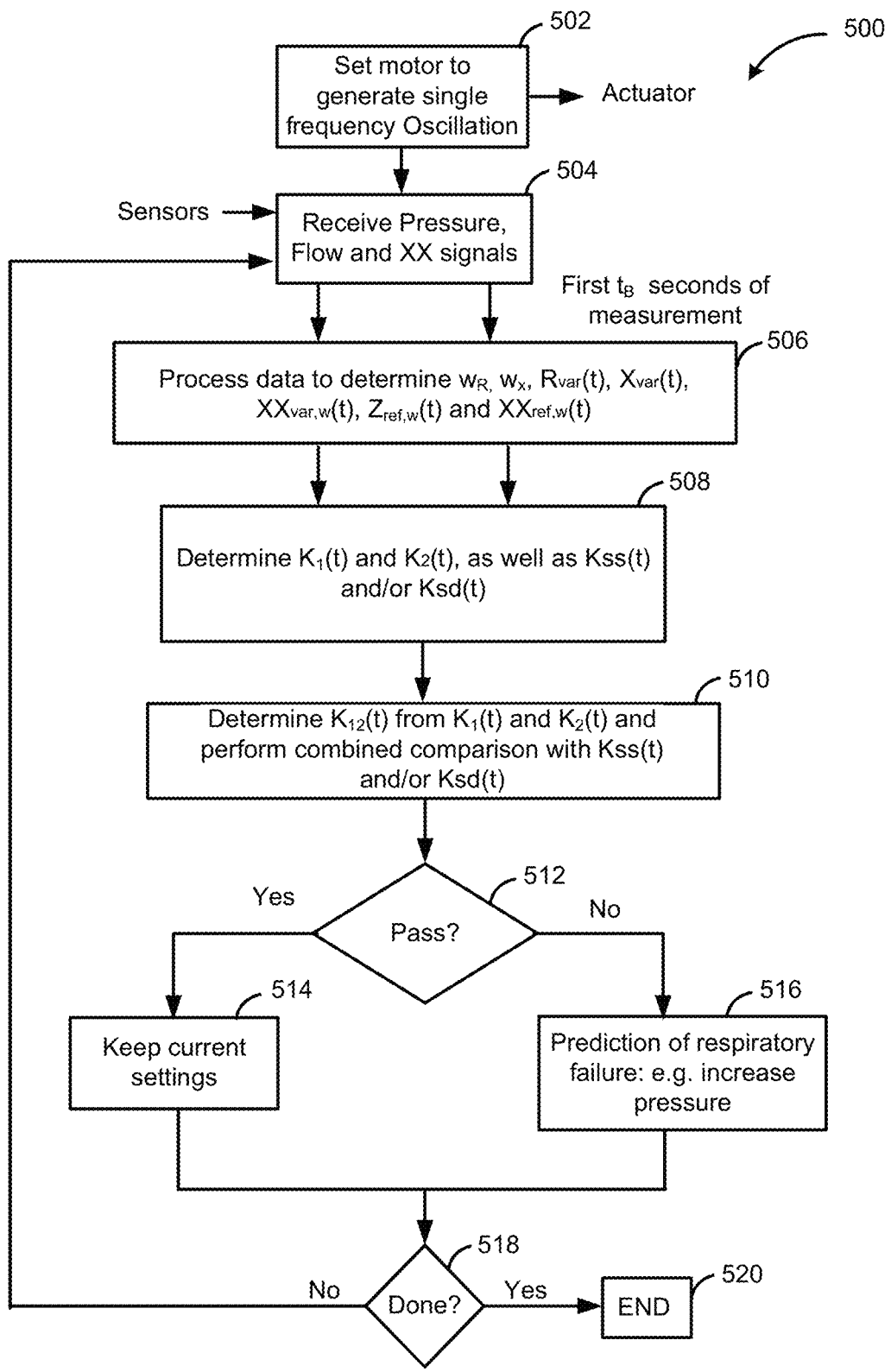
FIG. 8 is a flowchart of an example embodiment of a breathing assistance control method that utilizes respiratory failure prediction and at least one of a sleep stage classification index and a predicted sleep disruption severity index to adjust the settings of a breathing assistance device in accordance with the teachings herein.

Referring now to FIG. 8, shown therein is a flowchart depicting an example embodiment of a breathing assistance control method 500 that can be used to acquire pressure and airflow measurements and at least one other physiological measurement and use the measurements to predict when respiratory failure is occurring for a user and also incorporates a sleep stage classification index and/or a predicted sleep disruption severity index to take proactive action to control the operation of a breathing assistance device 202 to prevent the predicted respiratory failure from occurring. As in the description of FIG. 7, for ease of explanation, the elements depicted in the breathing assistance system 200 shall be used in describing the various steps of the method 500 for making predictions. For example, the method 500 may be implemented by the processor 228 of the breathing assistance system 200. However, it should be understood that this technique can be used on the integrated breathing assistance device controller 250 or another applicable device.

The method 500 begins in a similar fashion as the method 450 when the breathing assistance device 202 has been activated, and is supplying an airflow to the user 210. Act 502 is the same as act 302 for performing FOT and act 504 is similar to act 304, in that sensors, such as the flow transducer 220 and the pressure transducer 221, are used to measure the flow rate and pressure, respectively, of the airflow (including the perturbation) that is sent to the user 210 and these measured signals are preprocessed in a similar manner as those obtained at act 304. However, act 504 is different than act 304 in that act 504 also includes obtaining at least one PSG signal which is denoted by XX. The PSG signals XX include (a) CO2, O2 and/or some other gas in the user's expired breath, (b) the user's ECG (i.e. brain activity), (c) the user's EOG (i.e. eye movements), and/or (d) the user's EMG (i.e. skeletomuscular activity). These signals can be measured as described previously. The PSG signal(s) are now used in addition to the measurements of pressure and flow of breathing to predict respiratory failure. This is in contrast to the method 450 of FIG. 7 where only the measurement of pressure and flow of breathing were used to detect respiratory failure.

After the signals have been processed by applying amplification and filtering, the processed signals are received by the processor 228 for further processing and analysis. At act 506 the processor 228 may determine the volume V(t) of the airflow and the mechanical impedance of the user's respiratory system over time as was described for act 406 of method 450 in terms of using windows and frequency transforms for analyzing the data to obtain an estimate of the average mechanical impedance $Z_{rs}$ as well as the resistance $R_{rs}(t)$ and reactance $X_{rs}(t)$ for the various time windows of data that are analyzed. Act 506 also determines the weight parameters $w_R$ and $w_X$ for resistance and reactance, respectively, the baseline weighted impedance $Z_{ref,w}(t)$ and the current weighted impedance $Z_{var,w}(t)$ in the various time windows of data that are analyzed in a similar manner as was described for act 306. However, act 506 is different than act 306 in that act 506 also includes determining a baseline weighted PSG signal $XX_{ref,w}(t)$ and the current weighted PSG signal $XX_{var,w}(t)$ for the additional physiological and/or neurological signals XX. When the baseline weighted PSG signal $XX_{ref,w}(t)$ and the current weighted PSG signal $XX_{var,w}(t)$ are determined using at least two PSG signals, these PSG signals are combined in some fashion. For example, since there are multiple streams of time series data, the cross-correlation, the Cross-Spectral density or the Coherence of pairs of data streams can be determined providing a richer mode of analysis as this will indicate relationships between pairs of data streams. For example, in some embodiments, the coherence between pressure and flow data may yield a value between 0 and 1 which may be used as a time series data that can be used for further analysis.

The method 500 then proceeds to act 508 where continuous monitoring of the current weighted impedance $Z_{var,w}(t)$ and the current weighted PSG signal $XX_{var,w}(t)$ is performed while the method 500 is being implemented by the breathing assistance device 202 until the method ends at act 520. The current weighted impedance $Z_{var,w}(t)$ may be obtained according to equation (3). The current weighted PSG signal $XX_{var,w}(t)$ is obtained using the same equation as for $XX_{ref,w}(t)$ except that the calculations are done using data from the current time window.

Act 508 also includes determining values for a first time varying index $K_1(t)$ (i.e. a first index signal) that represents respiratory status and a second time varying index $K_2(t)$ (i.e. a second index signal) that represents PSG status. For example, the first index $K_1(t)$ may track the deviation of the current weighted impedance relative to the baseline weighted impedance according to equation (5). The second index $K_2(t)$ may track the deviation of the current weighted PSG signal relative to the baseline weighted PSG signal according to equation (6).

$$K_1(t) = \frac{\sum (Zvar, w(t) - Zref, w(t))^2}{\sum (Zref, w(t))^2} \quad (5)$$

$$K_2(t) = \frac{\sum (XXvar, w(t) - XXref, w(t))^2}{\sum (XXref, w(t))^2} \quad (6)$$

Equations (5) and (6) are provided as examples and there may be other techniques of determining the indices $K_1(t)$ and $K_2(t)$. Based on equations (5) and (6) $K_1(t)$ and $K_2(t)$ are normalized to have a magnitude that is less than or equal to 1. In other embodiments other equations can be used instead of equations (5) and (6) for determining the index signals $K_1(t)$ and $K_2(t)$. Act 508 also includes determining the Kss(t) and Ksd(t) as described for act 452.

The method 500 then proceeds to act 510 where the first and second index signals $K_1(t)$ and $K_2(t)$ are combined to create the respiratory index signal $K_{12}(t)$. The index signal $K_{12}(t)$ is combination of the weighted influence of varying impedance measurements and another PSG measurement. For example $K_1$ may be measured impedance and $K_2$ may be measured from EEG which are both taken into account when creating $K_{12}(t)$. This combination can be done according to equation (7a) or equation (7b).

$$K_{1,2}(t) = K_1(t) * K_2(t) \quad (7a)$$

$$K_{1,2}(t) = K_1(t)/(K_1(t) + K_2(t)) + K_2(t)/(K_1(t) + K_2(t)) \quad (7b)$$

Alternatively, the combination of $K_1(t)$ and $K_2(t)$ into $K_{1,2}(t)$ can be done using another technique. The respiratory index $K_{1,2}(t)$ is different from the respiratory index K(t) in that the respiratory index $K_{1,2}(t)$ is used in the prediction of respiratory failure while the respiratory index K(t) is used in the detection of respiratory failure. Act 510 also involves performing the combined comparison of one or more threshold values with $K_{1,2}(t)$ as well as Kss(t) and/or Ksd(t) using the technique described for method 450 at act 452 and a pass or fail is determined which is then considered at act 512 to determine the next act.

If there is a pass at act 512 then this indicates that the user 210 is not likely to be developing respiratory failure in the imminent future (e.g. in the next tens of seconds to a minute or so). In this case the method 500 proceeds to act 514 where the current settings for the breathing assistance device 202 are maintained.

However, if there is a fail at act 512 then it is predicted that the user 210 is likely to be developing respiratory failure in the imminent future (e.g. in the next tens of seconds to a minute or so). In this case, the method 500 proceeds to act 516 where the settings for the breathing assistance device 202 are changed to reduce the likelihood that the user 210 will experience the predicted respiratory failure. The adjustments may be made in various ways. For example, the amount of the adjustment may be based on the value of the predictive sleep disruptive severity index, and the amount of adjustment can be determined using experimental data as explained previously.

After the method 500 has performed act 514 or 516, the method 500 proceeds to act 518 where it is determined whether the method 500 is finished operating. If the condition at act 518 is true then the method 500 proceeds to act 520 and ends. If the condition at act 518 is not true then the method 500 goes to act 504 and continues to obtain sensor values, monitor the current weighted impedance and current weighted PSG, generate the two index values $K_1(t)$ and $K_2(t)$ and combine them into the respiratory index signal $K_{1,2}(t)$, generate Kss(t) and/or Ksd(t) and do the combined comparison with $K_{1,2}(t)$, and Kss(t) and/or Ksd(t) to predict when the user 210 is likely to soon experience respiratory failure and update the operation of the breathing assistance device 202 to avoid the predicted respiratory failure.

The weight parameters ($w_r$ and $w_x$) can reflect the specific portion of the reactive/elastic part of the user's respiratory system that is distancing or deviating itself from the elastic part and influencing the resistive part instead (e.g. sometimes because other factors are involved such as the fact that resistance and elastance themselves are sinusoidally changing with breathing, the multiplication of sinusoidal elastance and sinusoidal volume may change the phase of a portion of the elastance to become in phase with air flow, and hence be more resistive). The result of this deviation can cause distress for the user 210 since it may manifest physically as either an obstruction of their airways or a deep distress to their respiratory system due to various factors including, but not limited to, derecruitment of certain lung regions, increased heterogeneity of the user's lungs and/or the presence of liquid in the user's lungs. As such the determined parameters can thus be used to perform: (a) tuning of the breathing assistance device 202 to minimize respiratory failure; diagnosis or identification of the presence of respiratory disease; and/or (b) operating the breathing assistance device 202 to obtain therapeutic outcomes, for example, with respect to adjusting the operating parameters of the breathing assistance device 202 such as the pressure, the flow rate, and/or the moisture of the generated airflow to help COPD patients to breathe or expectorate.

Figure 9A:
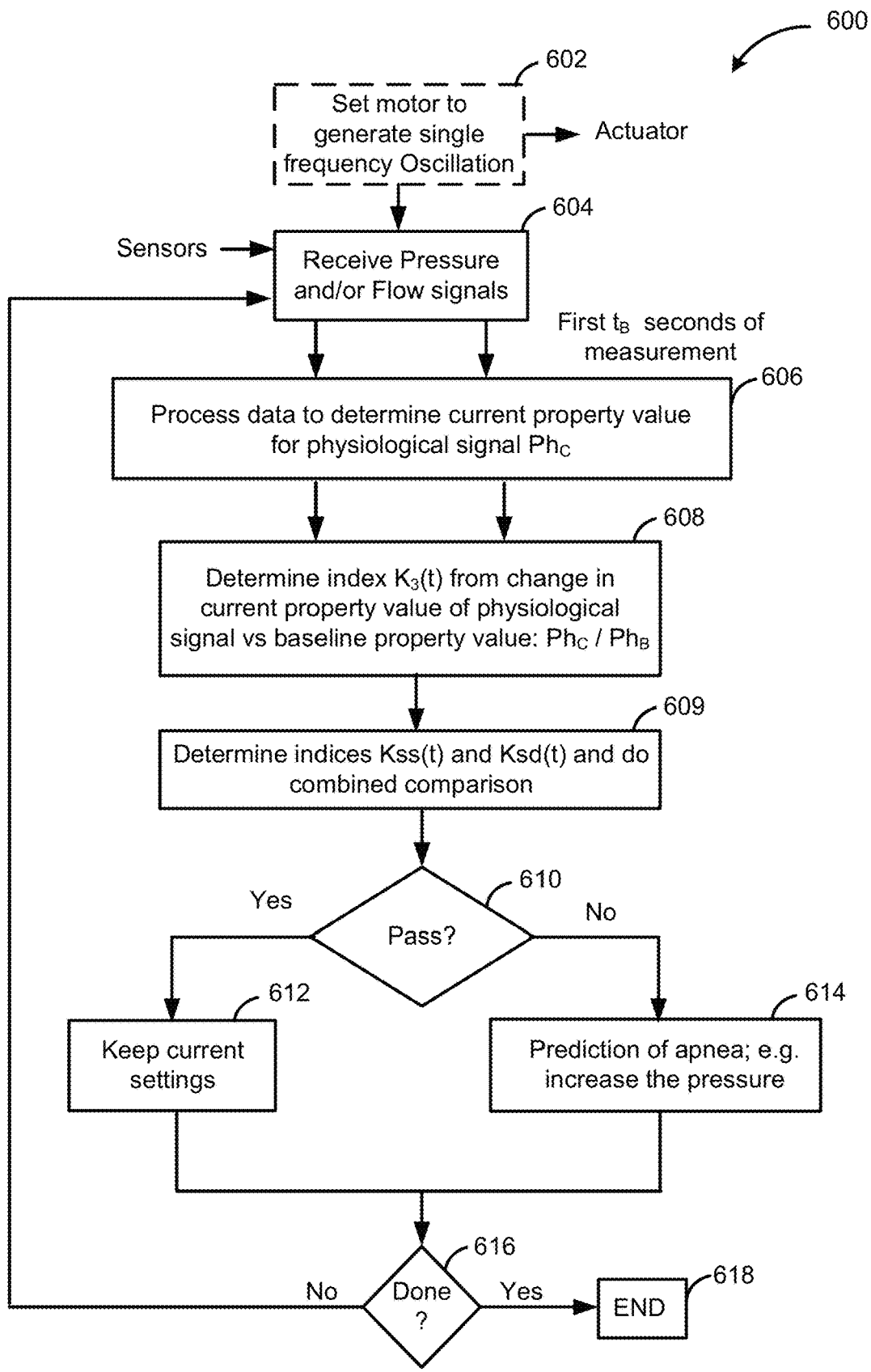
FIG. 9A is a flowchart of another example embodiment of a breathing assistance control method that utilizes respiratory failure prediction and at least one of a sleep stage classification index and a predicted sleep disruption severity index to adjust the settings of a breathing assistance device in accordance with the teachings herein.

Referring now to FIG. 9A, shown therein is a flowchart depicting another example embodiment of a breathing assistance control method 600 that can be used to acquire pressure and airflow measurements, to use the measurements along with the sleep stage classification index Kss(t) and/or the predicted sleep disruption severity index Ksd(t) to predict when respiratory failure is occurring for the user 210 and to take proactive action to control the operation of a breathing assistance device 202 to prevent the predicted respiratory failure from occurring. As in the description of the methods 450 and 500 of FIGS. 7 and 8, respectively, for ease of explanation, the elements depicted in the breathing assistance system 200 shall be used in describing the various steps of the method 600. It should be understood that the method 600 can be performed by the processor 228. However, it should be understood that this technique can be used on the integrated breathing assistance device controller 250 or another applicable device.

The method 600 begins in a similar fashion as methods 450 and 500 when the breathing assistance device 202 has been activated, and is supplying an airflow to the user 210. Act 602 is the same as acts 452 and 502 for performing FOT but it should be noted that act 602 may be optional when the physiological parameters being used to predict a respiratory failure do not need the FOT technique in order to be measured. For example, the physiological measurements that may be used with method 600 can be flow rate, pressure and/or tidal volume in which case the FOT method is not required and act 602 can be skipped. Alternatively, the physiological measurements that may be used with the method 600 may also be resistance, reactance and/or impedance in which case the FOT method of act 602 is performed.

Act 604 may be slightly different compared to act 304 in that it may include receiving just one of the pressure and flow signals rather than both of them depending on the physiological parameter which is being used to perform the respiratory failure prediction. For example, if pressure is being used to predict respiratory failure then only the pressure signal is measured and received. Alternatively, if physiological parameters like resistance, reactance and/or impedance are being used to predict respiratory failure then both the flow rate and the pressure signals are measured and received at act 604. In each of these case, the signals can be measured as described previously.

After the signals have been processed by applying amplification and filtering as required, as described earlier, the processed signals are received by the processor 228 for further processing and analysis. At act 606, the processor 228 determines a baseline value for the physiological parameter ($Ph_C$) for a certain period of time ($t_B$), such as about 1 seconds, about 2 seconds, about 5 seconds, or about 10 seconds, before the occurrence of a respiratory failure. This may be determined by performing sleep studies on the user 210, collecting a plurality of time segment data for determining the physiological parameter in which each time segment includes a baseline time period before the occurrence of a respiratory event, determining a baseline property value for a property of the physiological parameter and then during actual use determining a current property value for the property and comparing the current property value to the baseline property value to determine if there is a large enough change to predict that a respiratory failure is likely to be imminent.

The inventors have previously determined that the determination made at act 606 may be used to predict an imminent respiratory failure based on sleep study data obtained from patients including a first study using data from CPAP memory cards for 10 patients who suffer from severe sleep apnea including 8 males and 2 females with an overall average age of 53 years and a second study using data from 7 hospital patients who were all male, suffer from severe sleep apnea and have an overall average age of 51 years. For the second study group, all of the data were recorded for a single night so the number of sleep apnea events for the patients in the second study group were lower than the number of sleep apnea events in the data obtained from the CPAP memory cards; however, the data from the second study group contained FOT data for FOT tests that were continuously done during the one night test. While all of the data had sleep apnea events, it is believed that the findings are applicable to other types of respiratory failures. This is because it was generally found that there was a significant difference in spectral density characteristics in signals recorded previous to a respiratory failure occurring compared to signals recorded when breathing was healthy for different types of respiratory conditions. For example, this was found in airflow data and impedance data for patients that had sleep apnea as well as other patients that had other respiratory conditions such as expiratory flow limitation associated with COPD that was showing up both in airflow data and the impedance data.

In all of the examples given above, the relative power densities are determined for certain data over time windows of about 0.1 to about 60 seconds. The longer time windows are useful for cases where the data is more noisy. A time varying index $K_3(t)$ is then determined based on the relative power spectral density at act 608 and then combined with Ksd(t) and/or Kss(t) at act 609 to perform a combined comparison as described previously for act 452 of method 450 and the combined comparison can then be checked at act 610 for a pass or fail result. If the combined comparison indicates that it is not likely that there will be an imminent respiratory failure event then the method 600 proceeds to act 612 where the operating parameters of the breathing assistance device 202 are left the same. Otherwise if the comparison indicates that it is likely that there will be an imminent respiratory failure event then the method 600 proceeds to act 614 where the operating parameters of the breathing assistance device 202 are adjusted (as explained previously) to avoid or reduce the likelihood that the respiratory failure will occur. The amount of the adjustment may be based on the value of the predictive sleep disruptive severity index as was described previously.

It should be noted that at act 608 where the power spectral density is determined, this can be done in a variety of ways. For example, the Welch method, may be used to decompose the power spectral density of the recorded signals. As described, comparing the power spectral density at time points that are distant from a respiratory failure versus time points that imminently precede the respiratory failure event, the power of some frequency components consistently decreases about 30 seconds before the respiratory failure event takes place.

In another example embodiment, the Fast Fourier transform can be used to obtain the power spectral density values. Alternatively, a Constant-Q transform may be used which may be advantageous since the power of the recorded data tapers off approximately following a 1/f scaling law and thus absolute power is considerably much lower at higher frequencies, making relative changes in power highly variable. Using a parameterization which is logarithmic in frequency, such as the Constant-Q transform, may provide more stable power estimates, since power will be logarithmically spaced (instead of linearly spaced, as per the FFT method).

Figure 9B:
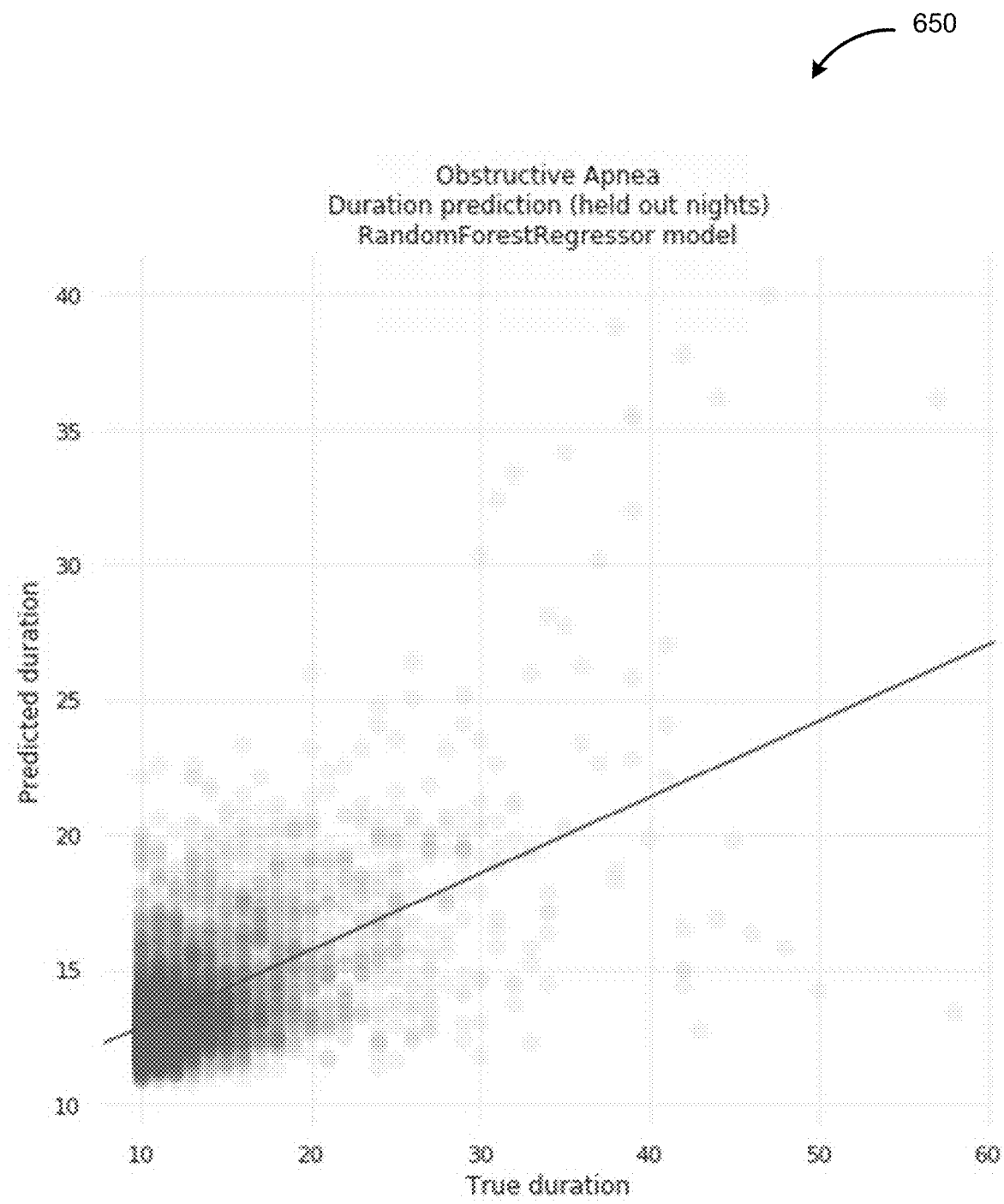
FIG. 9B is a plot of the correlation between the predicted duration/intensity and actual true duration/intensity of apnea events.

Referring now to FIG. 9B, shown therein is a plot of the correlation between the predicted duration/intensity and actual true duration/intensity of apnea events. The data was obtained over a period of 4,290 nights from 25 patients. The machine learning model that was employed was a Random Forest model, consisting of an ensemble of 1,000 decision trees each of which was trained on a random bootstrap of the 21,772 training samples (samples were drawn with replacement 21,772 times for each decision tree). The input features that can be used may be like those in the description of the machine learning models 229f. The model was trained to minimize the mean squared error of the predicted apnea duration. Validation was performed using 931 nights of held out data containing 5,088 obstructive apneas and a mean absolute error of 2.72 s was obtained. About 31.2% of the variance in the apnea durations can be explained by using the following equation:

$$\text{explained\_variance} = 1 - \text{Var}(y - y\_\text{predicted})/\text{Var}(y) \quad (8).$$

The explained variation measures the proportion to which a mathematical model accounts for the variation. The straight line in FIG. 9B is a line of best fit to show the correlation between the model's output and the true values.

It should be noted that in the various detection and prediction methods described herein that other weighted measures can be used based on the XX, $R_{var}$, $X_{var}$, $XX_{var}$ and $Ph_C$ signals for each monitoring time period and that $Z_{var,w}$, $Z_{ref,w}$, $XX_{var,w}$, $XX_{ref,w}$ and $Ph_C$ are given as examples. Therefore, the measures of baseline weighted impedance and current weighted impedance may be more generally referred to as a baseline weighted respiratory status value and a current weighted respiratory status value that are each determined using $X_{var}$ and $R_{var}$ over a corresponding monitoring time period.

As previously proven by the inventors, in another aspect, at least one of the embodiments of the breathing assistance device controller and/or systems described herein that utilize the breathing assistance device controller 206 may be further simplified by operating at a single frequency. Although known single frequency FOT machines commonly operate at a frequency close to breathing (e.g. 4-5 Hz), the various embodiments described herein can operate at a higher frequency which allows for the use of a smaller, lighter actuator 216, that enables the breathing assistance device controller to have lower power consumption, more precise signal processing and a smaller footprint so that it can more easily be used with existing breathing assistance devices in an inline fashion. This is because higher frequencies are not contaminated as much by breathing noise which leads to higher Signal to Noise Ratio (SNR). Consequently, the required amplitude of oscillation of the air pressure perturbation that is sent to the user 210 becomes smaller and may be provided by an actuator that is smaller and lighter and perhaps cheaper. Furthermore, using a higher frequency of oscillation also reduces the discomfort that the user (e.g. patient) receives from sensing vibrations in the airflow that is provided to them.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

The invention claimed is:

1. A controller for controlling an operation of a breathing assistance device that provides breathing assistance to a user, wherein the controller comprises:
   a memory unit that comprises software instructions and parameters for at least one machine learning model and a sleep disruption severity predictor; and
   a processor that is electronically coupled to one or more sensors, the processor being configured to perform measurements and to generate a control signal for controlling the breathing assistance device for a current monitoring time period by:
   receiving sensor data obtained by the one or more sensors, the sensor data corresponding to measurements of at least one airflow parameter of the user's airflow;
   obtaining, from the sensor data, measured air pressure data, measured airflow data or both the measured air pressure data and the measured airflow data during the current monitoring time period when the user is using the breathing assistance device;
   performing feature extraction on the measured air pressure data, the measured airflow data or both the measured air pressure data and the measured airflow data to obtain feature values;
   applying a predictive sleep disruption severity machine learning model to the feature values and using the sleep disruption severity predictor to determine a predictive sleep disruption severity index for the user to predict a severity of an upcoming sleep disruption event; and adjusting the control signal of the breathing assistance device based on at least the predicted sleep disruption severity index.

2. The controller of claim 1, wherein the predictive sleep disruption index is generated to have a value or a class that is indicative of an amount of sleep disruption severity.

3. The controller of claim 1, wherein the predictive sleep disruption index is generated to have a class that is indicative of a length of a predicted sleep apnea event.

4. The controller of claim 1, wherein the control signal of the breathing assistance device is configured to increase air pressure from the breathing assistance device to the user by a first amount when the sleep disruption severity index is at a low value and by a second amount when the sleep disruption severity index is at a higher level, where the second amount is higher than the first amount.

5. The controller of claim 1, wherein the feature values are additionally determined from calculated airway impedance that is determined using one or multi-frequency Forced Oscillation Technique (FOT).

6. The controller of claim 5, wherein FOT data is measured and used to determine the predicted sleep disruption severity index.

7. The controller of claim 1, wherein the predictive sleep disruption severity machine learning model is initially based on a base model and is updated with adjusted features for the user to increase accuracy.

8. The controller of claim 1, wherein the processor is configured to execute a breathing signature classifier that applies a breathing signature machine learning model to the feature values to determine a current breathing signature for the user.

9. The controller of claim 8, wherein the processor is configured to stop operation of the breathing assistance device when the current breathing signature does not match a stored breathing signature for a rightful user of the breathing assistance device.

10. The controller of claim 1, wherein the processor is configured to:
    determine an index signal of the user;
    execute a sleep stage classifier that applies a sleep stage machine learning model to the feature values to determine a sleep stage classification index for the user;
    determine whether the user is experiencing a respiratory failure or that a respiratory failure is predicted to occur based on the index signal, the sleep stage classification index and the predicted sleep disruption severity index; and
    change the settings for the breathing assistance device when the user is experiencing the respiratory failure or the respiratory failure is predicted to occur so that the user's respiratory health improves.

11. The controller of claim 10, wherein the processor is configured to determine whether the user is experiencing the respiratory failure or that the respiratory failure is predicted to occur by comparing the sleep stage classification index and the predicted sleep disruption severity index to respective thresholds.

12. The controller of claim 10, wherein the processor is configured to determine whether the user is experiencing the respiratory failure or that the respiratory failure is predicted to occur by combining the sleep stage classification index and the predicted sleep disruption severity index to generate a combined index according to a mathematical mapping function and comparing the combined index to a threshold.

13. The controller of claim 10, wherein the processor is configured to determine the index signal using a respiratory index signal based on a combination of a baseline weighted impedance and a current weighted impedance of a respiratory system of the user.

14. The controller of claim 10, wherein the processor is configured to determine the index signal based on a combination of a first time varying index that represents respiratory status and a second time varying index that represents polysomnography (PSG) status.

15. The controller of claim 14, wherein the processor is configured to use at least one polysomnography (PSG) signal to determine the second time varying index that represents the PSG status, where the at least one polysomnography signal includes one or more of (a) a measure of $CO_2$, $O_2$ and/or other gas in an expired breath of the user, (b) an ECG signal of the user, (c) an EOG signal of the user, and/or (d) an EMG signal of the user.

16. The controller of claim 15, wherein when the at least one polysomnography signal includes at least two PSG signals, time series data for the at least two PSG signals are combined to determine the baseline weighted impedance and the current weighted impedance where the combining is done using cross-correlation, cross-spectral density or coherence of pairs of data streams.

17. The controller of claim 10, wherein the index signal is determined from relative power spectral densities of the measured air flow or airway impedance over time windows of about 0.1 to about 60 seconds.

18. The controller of claim 1, wherein the breathing assistance device comprises one of a mechanical ventilator, a CPAP, APAP, BiPAP or PAP device, a respiratory treatment delivery device that assists a user in clearing their lungs and coughing out secretions, an anesthesia machine in an Operating Room (OR), an Intensive Care Unit (ICU) ventilator, or a home ventilator and oxygenator of COPD.

19. A system for providing breathing assistance to a user, wherein the system comprises:
    a breathing assistance device that generates an airflow comprising at least one pressure pulse or a continuous pressure flow rate;
    an entry element that is coupled to the breathing assistance device and is configured to be worn by the user to provide the airflow to the user during use; and
    the breathing assistance device controller that is defined according to claim 1.

20. A method for adjusting an airflow provided by a breathing assistance device to a user, wherein the method comprises:
    receiving sensor data corresponding to measurements of at least one airflow parameter of the user's airflow;
    receiving the sensor data at a processor, and using the processor for executing software instructions and parameters for at least one machine learning model and a sleep disruption severity predictor, performing measurements and generating a control signal for controlling the breathing assistance device for a current monitoring time period by:
    obtaining, from the sensor data, measured air pressure data, and/or measured airflow data or both the measured air pressure data and the measured airflow data during the current monitoring time period when the user is using the breathing assistance device;
    performing feature extraction on the measured air pressure data, the measured airflow data or both the measured air pressure data and the measured airflow data to obtain feature values;

applying a predictive sleep disruption severity machine learning model to the feature values to determine a predictive sleep disruption severity index for the user to predict a severity of an upcoming sleep disruption event; and
adjusting the control signal of the breathing assistance device based on at least the predicted sleep disruption severity index.

* * * * *

UNITED STATES PATENT AND TRADEMARK OFFICE
CERTIFICATE OF CORRECTION

PATENT NO. : 11,612,708 B2
APPLICATION NO. : 17/726719
DATED : March 28, 2023
INVENTOR(S) : Hamed Hanafialamdari et al.

Page 1 of 1

It is certified that error appears in the above-identified patent and that said Letters Patent is hereby corrected as shown below:

In the Claims

Claim 20, Column 40, Line 60, "...data, and/or measured airflow data..." should read -- "data, measured airflow data" --

Signed and Sealed this
Eighteenth Day of July, 2023

Katherine Kelly Vidal
*Director of the United States Patent and Trademark Office*